United States Patent
Li et al.

(10) Patent No.: US 12,018,333 B2
(45) Date of Patent: Jun. 25, 2024

(54) METHOD AND KIT FOR IDENTIFYING LUNG CANCER STATUS

(71) Applicant: Excellen Medical, Changping District Beijing (CN)

(72) Inventors: Mingming Li, Changping District Beijing (CN); Shuyu Li, Changping District Beijing (CN); Yanli Chen, Changping District Beijing (CN); Chunye Xu, Changping District Beijing (CN); Jue Pu, Changping District Beijing (CN)

(73) Assignee: Excellen Medical, Changping District Beijing (CN)

( * ) Notice: Subject to any disclaimer, the term of this patent is extended or adjusted under 35 U.S.C. 154(b) by 340 days.

(21) Appl. No.: 16/964,159

(22) PCT Filed: Jan. 23, 2018

(86) PCT No.: PCT/CN2018/073817
§ 371 (c)(1),
(2) Date: Jul. 22, 2020

(87) PCT Pub. No.: WO2019/144275
PCT Pub. Date: Aug. 1, 2019

(65) Prior Publication Data
US 2021/0032704 A1 Feb. 4, 2021

(51) Int. Cl.
*C12Q 1/68* (2018.01)
*C12Q 1/6806* (2018.01)
(Continued)

(52) U.S. Cl.
CPC ......... *C12Q 1/6886* (2013.01); *C12Q 1/6806* (2013.01); *C12Q 1/6818* (2013.01);
(Continued)

(58) Field of Classification Search
None
See application file for complete search history.

(56) References Cited

U.S. PATENT DOCUMENTS

| 2011/0245087 A1* | 10/2011 | Weiss | C12Q 1/6886 |
| | | | 506/7 |
| 2013/0022974 A1* | 1/2013 | Chinnaiyan | C12Q 1/6886 |
| | | | 435/6.11 |

(Continued)

FOREIGN PATENT DOCUMENTS

| CN | 101705291 A | 5/2010 |
| CN | 101365806 B | 11/2016 |

(Continued)

OTHER PUBLICATIONS

Zhang, C. et al., DNA Methylation Analysis of the SHOX2 and RASSF1A Panel in Bronchoalveolar Lavage Fluid for Lung Cancer Diagnosis, J. Cancer, vol. 8, pp. 3585-3591 (Year: 2017).*

(Continued)

*Primary Examiner* — Aaron A Priest
(74) *Attorney, Agent, or Firm* — TraskBritt

(57) ABSTRACT

A method for identifying lung cancer status in a subject comprising: collecting a biological sample from the subject; detecting the methylation level of a biomarker gene in the biological sample, the biomarker gene being one or more selected from the following genes: BCAT1, CDH1, DCLK1, FOXL2, HOXA9, PTGER4, RARB, RASSF1A, Septin9, and SHOX2; and comparing the detected methylation levels with a normal methylation level of a corresponding biomarker gene in the population to determine the lung cancer status in the subject. Also provided herein is a kit for identifying lung cancer status in a subject.

7 Claims, 6 Drawing Sheets
Specification includes a Sequence Listing.

(51) Int. Cl.
C12Q 1/6818 (2018.01)
C12Q 1/686 (2018.01)
C12Q 1/6886 (2018.01)

(52) U.S. Cl.
CPC ....... *C12Q 1/686* (2013.01); *C12Q 2523/125* (2013.01); *C12Q 2600/154* (2013.01)

(56) References Cited

U.S. PATENT DOCUMENTS

| | | | | |
|---|---|---|---|---|
| 2014/0045915 | A1* | 2/2014 | Skog | C12Q 1/6806 435/15 |
| 2016/0340740 | A1* | 11/2016 | Zhang | C12Q 1/6883 |
| 2017/0335401 | A1 | 11/2017 | Allawi et al. | |
| 2019/0010541 | A1* | 1/2019 | Menschikowski ... | C12Q 1/6851 |
| 2019/0241963 | A1* | 8/2019 | Rurup | C12Q 1/6806 |
| 2020/0157633 | A1* | 5/2020 | Regev | A61K 31/475 |

FOREIGN PATENT DOCUMENTS

| | | | | |
|---|---|---|---|---|
| CN | 106232833 | A | 12/2016 | |
| CN | 104745681 | | 11/2018 | |
| EP | 3190191 | A1 | 7/2017 | |
| WO | WO-2008122447 | A2 * | 10/2008 | ........... C12Q 1/6886 |
| WO | WO-2012087983 | A1 * | 6/2012 | ........... C12N 15/113 |
| WO | WO-2014020124 | A1 * | 2/2014 | ........... C12Q 1/6846 |
| WO | 2015/187823 | A2 | 12/2015 | |
| WO | 2016/166124 | A1 | 10/2016 | |

OTHER PUBLICATIONS

Hoang, P.H. et al., DNA Methylation in Lung Cancer: Mechanisms and Associations with Histological Subtypes, Molecular Alterations, and Major Epidemiological FactorsCancers, vol. 14: 961, pp. 1-23 (Year: 2022).*

Constancio, V. et al., DNA Methylation-Based Testing in Liquid Biopsies as Detection and Prognostic Biomarkers for the Four Major Cancer Types, Cells, vol. 9: 624, pp. 1-32 (Year: 2020).*
Hernandez et al., Optimizing methodologies for PCR-based DNA methylation analysis, Biotechniques, vol. 55, pp. 181-197 (Year: 2013).*
Cottrell, S.E. et al., A real-time PCR assay for DNA-methylation using methylation-specific blockers, Nucl. Acids Res., vol. 32, e10, pp. 1-8 (Year: 2004).*
International Search Report for International Application No. PCT/CN2018/073817 dated Oct. 29, 2018, 3 pages.
International Written Opinion for International Application No. PCT/CN2018/073817 dated Oct. 29, 2018, 4 pages.
European Extended Supplementary Search Report and Opinion for European Application No. 18902313, dated Dec. 10, 2021, 13 pages.
Josep et al., "Translating cancer epigenomics into the clinic: focus on lung cancer", Translational Research, vol. 189, Nov. 2017, pp. 76-92.
Lagares et al., "A Novel Epigenetic Signature for Early Diagnosis in Lung Cancer", Clinical Cancer Research, vol. 22, No. 13, Feb. 3, 2016, 3361-3371.
People's Republic of China Medical Device Registration Certificate (IVD Reagents), Registration Certificate No. 20223400203 dated Feb. 15, 2022, 2 pages.
TUVRheinland, CE Technical Documentation Review Report, Diagnostic Kit for Methylated Genes of Lung Cancer (Real Time PCR), Report No. 60389452-001, Nov. 22, 2020, 1 page.
Gu et al., Methylation in Lung Cancer: A Brief Review, Methods in Molecular Biology, vol. 2204, (2020), https://doi.org/10.1007/978-1-0716-0904-0_8, 7 pages.
Klein et al., Clinical Validation of a Targeted Methylation-Based Multi-Cancer Early Detection Test Using an Independent Validation Set, https://doi.org/10.1016/j.annonc.2021.05.806, Annals of Oncology, vol. 32, Issue 9, (2021), pp. 1167-1177.

* cited by examiner

```
                        SEQUENCE LISTING

<160> NUMBER OF SEQ ID NOS: 101

<210> SEQ ID NO 1
<211> LENGTH: 279
<212> TYPE: DNA
<213> ORGANISM: Homo sapiens

<400> SEQUENCE: 1
cggacaaaac cataagtagt taccttcatt gttccgtcgg ccacgaggga agctcgagct      60
gagcggaggg cagatcccaa gggtcgtagc ccctggccgt gtggaccggg tctgcggctg     120
cagagcgcgg tcccggctgc agcaagacct ggggcagtgc ccgaggcggc ggcgagtaca     180
cgtggcgggc tggattgcag accggccctc tcgcggcgga gactcgcgac ctagcggatt     240
gcatcagcag gaagacacta aggctgctcc cccaggccg                            279

<210> SEQ ID NO 2
<211> LENGTH: 360
<212> TYPE: DNA
<213> ORGANISM: Homo sapiens

<400> SEQUENCE: 2
attcgaaccc agtggaatca gaaccgtgca ggtcccataa cccacctaga ccctagcaac      60
tccaggctag agggtcaccg cgtctatgcg aggccgggtg ggcgggccgt cagctccgcc     120
ctggggaggg gtccgcgctg ctgattggct gtggccggca ggtgaaccct cagccaatca     180
gcggtacggg gggcggtgcc tccggggctc acctggctgc agccacgcac ccctctcag      240 tggcgtcgga actgcaaagc acctgtgagc ttgcggaagt cagttcagac tccagcccgc     300
tccagcccgg cccgacccga ccgcacccgg cgcctgccct cgctcggcgt ccccggccag     360

<210> SEQ ID NO 3
<211> LENGTH: 690
<212> TYPE: DNA
<213> ORGANISM: Homo sapiens

<400> SEQUENCE: 3
gaggtttagg ggtgtagtca agccagatgc accgaggttg ctgcggtggg aagagggcgc      60
tgggagggag gaggacctgg ggcgcagccg tggtgggtgc gccctgccaa gaagggcggg     120
ggcgacgggg cgcgcacgcg gaggaggagg aggaggaggg agacgggagg gcgtgtgagc     180
gagtgagaca agaaaaggga gcgcgcccgc cgccgccgcc gccgccgccc tcctctggag     240
agagaggctg gagtgaggct gtgcgaagcg ccgcatttca atgaggacgg gccgaggcac     300
```

| | |
|---|---|
| atccctgcac tagtggccgc aaccgaggcg ccgcgctcca gcagctgctg ccgcccagcc | 360 |
| cggccccgcc gccgccccc agccctgcag ccccgcagcc ccggccgcgc ccagcccggc | 420 |
| gaggacagca ccaggaggcg ccccagcg cggccacaaa accccggc ggcgtctctc | 480 |
| cgcggaccgg tgcgtggttt gccttccctg gggacgggag ctgcggggag gcggccgggg | 540 |
| ggactccgca gagcccgctc cgcccgcagc cgcggggcgc cgagggcagg gcgggcgctc | 600 |
| agcttggccc cgccgccccg cccgcagttc ctcgaaaggc ggccgccctg ccctggccag | 660 |
| cctggcccga cccggggggcg ttgcgtgcgg | 690 |

```
<210> SEQ ID NO 4
<211> LENGTH: 475
<212> TYPE: DNA
<213> ORGANISM: Homo sapiens

<400> SEQUENCE: 4
```

| | |
|---|---|
| tgcggggaaa ggttttttaa aactcggttt catactatta ttattactaa ggacaaccgg | 60 |
| gcaggctgag gtcccaacgt ggatgatccg agttggcctc cgccggggc tctgcagcca | 120 |
| ctgccctgtg cgctcagcac ctctggggc gatcagggcc cctgcgcttc cgcccgccgc | 180 |
| ccggcagtcg agagcaccct gtgcccagac tggccgactc attctccccc gaattttgtt | 240 |
| tagagctggc aaggggact tagctcgcgc cccaagacct gggcttgcag cgccgccaac | 300 |
| aggcccgggg acacgaggcg ctccaggcg gggtcttccc ggctgctggc ccctctcgct | 360 |
| ccccacccgc tggcggcgcc tcggtcgccc gcaattgacc caacccgctt cctgcgtttg | 420 |
| cccctcaggt ttcccgtttc tccacaaagg cctagggag cctcgcccac aggct | 475 |

```
<210> SEQ ID NO 5
<211> LENGTH: 353
<212> TYPE: DNA
<213> ORGANISM: Homo sapiens

<400> SEQUENCE: 5
```

| | |
|---|---|
| aggtttaatg ccataaggcc ggctggaggg caagcccgcg aaggagagcg caccgggcgt | 60 |
| gggctccagc caggagcgca tgtacctgcc gtccggcgcc ccgccgcca cgggcgcctg | 120 |
| ggggtgcacg taggggtggt ggtgatggtg gtggtacacc gcagcgggta cagcgttggc | 180 |
| gcccgccgcg tgcactgggt tccacgaggc gccaaacacc gtcgccttgg actgaaagct | 240 |
| gcacgggctg aagtcggggt gctcggccag cgtcgccgcc tgccggggag ctggcccag | 300 |
| ggtccccggc gcatagcggc caacgctcag ctcatccgcg gcgtcggcgc cca | 353 |

```
<210> SEQ ID NO 6
<211> LENGTH: 450
<212> TYPE: DNA
<213> ORGANISM: Homo sapiens

<400> SEQUENCE: 6
```

| | |
|---|---|
| cttcttcagc ctgtccggcc tcagcatcat ctgcgccatg agtgtcgagc gctacctggc | 60 |
| catcaaccat gcctatttct acagccacta cgtggacaag cgattggcgg gcctcacgct | 120 |
| cttttgcagtc tatgcgtcca acgtgctctt ttgcgcgctg cccaacatgg gtctcggtag | 180 |
| ctcgcggctg cagtacccag acacctggtg cttcatcgac tggaccacca acgtgacggc | 240 |
| gcacgccgcc tactcctaca tgtacgcggg cttcagctcc ttcctcattc tcgccaccgt | 300 |
| cctctgcaac gtgcttgtgt gcggcgcgct gctccgcatg caccgccagt tcatgcgccg | 360 |
| cacctcgctg ggcaccgagc agcaccacgc ggccgcggcc gcctcggttg cctcccgggg | 420 |

```
ccaccccgct gcctccccag ccttgccgcg                                    450
```

<210> SEQ ID NO 7
<211> LENGTH: 828
<212> TYPE: DNA
<213> ORGANISM: Homo sapiens

<400> SEQUENCE: 7

```
acagacagaa aggcgcacag aggaatttaa agtgtgggct ggggggcgag gcggtgggcg    60
ggaggcgagc gggcgcaggc ggaacaccgt tttccaagct aagccgccgc aaataaaaag   120
gcgtaaaggg agagaagttg gtgctcaacg tgagccagga gcagcgtccc ggctcctccc   180
ctgctcattt taaaagcact tcttgtattg ttttttaaggt gagaaatagg aagaaaacg   240
ccggcttgtg cgctcgctgc ctgcctctct ggctgtctgc ttttgcaggg ctgctgggag   300
ttttttaagct ctgtgagaat cctgggagtt ggtgatgtca gactagttgg gtcatttgaa   360
ggttagcagc ccgggtaggg ttcaccgaaa gttcactcgc atatattagg caattcaatc   420
tttcattctg tgtgacagaa gtagtaggaa gtgagctgtt cagaggcagg agggtctatt   480
cttttgccaaa gggggacca gaattccccc atgcgagctg tttgaggact gggatgccga   540
gaacgcgagc gatccgagca gggtttgtct gggcaccgtc ggggtaggat ccggaacgca   600
ttcggaaggc tttttgcaag catttacttg gaaggagaac ttgggatctt tctgggaacc   660
ccccgccccg gctggattgg ccgagcaagc ctggaaaatg gtaaatgatc atttggatca   720
attacaggct tttagctggc ttgtctgtca taattcatga ttcggggctg ggaaaaagac   780
caacagccta cgtgccaaaa aaggggcaga gtttgatgga gttgggtg               828
```

<210> SEQ ID NO 8
<211> LENGTH: 443
<212> TYPE: DNA
<213> ORGANISM: Homo sapiens

<400> SEQUENCE: 8

```
ctgcgagagc gcgcccagcc ccgccttcgg gccccacagt ccctgcaccc aggtttccat    60
tgcgcggctc tcctcagctc cttcccgccg cccagtctgg atcctggggg aggcgctgaa   120
gtcgggccc gccctgtggc cccgccggc ccgcgcttgc tagcgcccaa agccagcgaa    180
gcacgggccc aaccgggcca tgtcggggga gcctgagctc attgagctgc gggagctggc   240
acccgctggg cgcgctggga agggccgcac ccggctggag cgtgccaacg cgctgcgcat   300
cgcgcggggc accgcgtgca accccacacg gcagctggtc cctggccgtg ccaccgcttt   360
ccagcccgcg gggcccgcca cgcacacgtg gtgcgacctc tgtggcgact tcatctgggg   420
cgtcgtgcgc aaaggcctgc agt                                           443
```

<210> SEQ ID NO 9
<211> LENGTH: 572
<212> TYPE: DNA
<213> ORGANISM: Homo sapiens

<400> SEQUENCE: 9

```
cggtgcgggt gcgggaacct gatccgcccg ggaggcgggg gcggggcggg ggcgcagcgc    60
gcggggaggg gccggcgccc gccttcctcc cccattcatt cagctgagcc agggggccta   120
ggggctcctc cggcggctag ctctgcactg caggagcgcg ggcgcggcgc ccagccagc   180
gcgcagggcc cgggccccgc cggggcgct tcctcgccgc tgccctccgc gcgacccgct    240
```

```
gcccaccagc catcatgtcg acccccgcgg tcaacgcgca gctggatggg atcatttcgg      300
acttcgaagg tgggtgctgg gctggctgct gcggccgcgg acgtgctgga gaggaccctg      360
cgggtgggcc tggcgcggga cggggtgcg ctgaggggag acgggagtgc gctgaggga      420 gacgggaccc ctaatccagg cgccctcccg ctgagagcgc cgcgcgcccc cggcccgtg      480 cccgcgccgc ctacgtgggg gaccctgtta ggggcacccg cgtagaccct gcgcgccctc      540
acaggaccct gtgctcgttc tgcgcactgc cg                                    572

<210> SEQ ID NO 10
<211> LENGTH: 490
<212> TYPE: DNA
<213> ORGANISM: Homo sapiens

<400> SEQUENCE: 10
tggctctctg cctaccgcaa acttgctggt ctaatttagg aacaattggg ccgaaaggta      60
tcagcgagag caacagaccc cggtgttgtg ccgcacaggg agccgcatcc gcagacgccc     120
ctcgctgccc ctgggctcgg gccaaaccct gcataaggtc ccctggacag ccaggtaatc     180
tccgtcccgc ctgcccgacc ggggtcgcac gagcacaggc gcccacgcca tgttggctgc     240
ccaaagggct cgccgcccaa gccgggccag aaggcaggag gcggaaaacc agcctccggt     300
ggcgggcgaa agcaaccgct ctttctgttc tctcttcgcc ctccctcgtg gaaacgcaga     360
ctcgacccta aacgcttaac ccacagagat caacaggttc aagcgaaata ttcgcgatcc     420
tcggtttcta ttggttgctc aaagcctttt catgcaacca gcagctcgga tgtttaataa     480
aatatgaatt                                                            490

<210> SEQ ID NO 11
<211> LENGTH: 24
<212> TYPE: DNA
<213> ORGANISM: Artificial Sequence
<220> FEATURE:
<223> OTHER INFORMATION: BCAT1 primer set 1 - primer 1

<400> SEQUENCE: 11
tgttgatgta attcgttagg tcgc                                             24

<210> SEQ ID NO 12
<211> LENGTH: 19
<212> TYPE: DNA
<213> ORGANISM: Artificial Sequence
<220> FEATURE:
<223> OTHER INFORMATION: BCAT1 primer set 1 - primer 2

<400> SEQUENCE: 12
aatacccgaa acgacgacg                                                   19

<210> SEQ ID NO 13
<211> LENGTH: 32
<212> TYPE: DNA
<213> ORGANISM: Artificial Sequence
<220> FEATURE:
<223> OTHER INFORMATION: BCAT1 primer set 1 - blocking primer

<400> SEQUENCE: 13
atttgttagg ttgtgagttt ttgttgtgag ag                                    32

<210> SEQ ID NO 14
<211> LENGTH: 22
<212> TYPE: DNA
<213> ORGANISM: Artificial Sequence
```

```
<220> FEATURE:
<223> OTHER INFORMATION: BCAT1 primer set 1 - probe

<400> SEQUENCE: 14
aaaccgaccc tctcgcgacg aa                                              22

<210> SEQ ID NO 15
<211> LENGTH: 21
<212> TYPE: DNA
<213> ORGANISM: Artificial Sequence
<220> FEATURE:
<223> OTHER INFORMATION: BCAT1 primer set 2 - primer 1

<400> SEQUENCE: 15
tttattgttt cgtcggttac g                                               21

<210> SEQ ID NO 16
<211> LENGTH: 20
<212> TYPE: DNA
<213> ORGANISM: Artificial Sequence
<220> FEATURE:
<223> OTHER INFORMATION: BCAT1 primer set 2 - primer 2

<400> SEQUENCE: 16
cccaaatctt actacaaccg                                                 20

<210> SEQ ID NO 17
<211> LENGTH: 31
<212> TYPE: DNA
<213> ORGANISM: Artificial Sequence
<220> FEATURE:
<223> OTHER INFORMATION: BCAT1 primer set 2 - blocking primer

<400> SEQUENCE: 17
tgttggttat gagggaagtt tgagttgagt g                                    31

<210> SEQ ID NO 18
<211> LENGTH: 23
<212> TYPE: DNA
<213> ORGANISM: Artificial Sequence
<220> FEATURE:
<223> OTHER INFORMATION: BCAT1 primer set 2 - probe

<400> SEQUENCE: 18
cgcgctctac aaccgcaaac ccg                                             23

<210> SEQ ID NO 19
<211> LENGTH: 25
<212> TYPE: DNA
<213> ORGANISM: Artificial Sequence
<220> FEATURE:
<223> OTHER INFORMATION: CDH1 primer set 1 - primer 1

<400> SEQUENCE: 19
cgaatttagt ggaattagaa tcgtg                                           25

<210> SEQ ID NO 20
<211> LENGTH: 19
<212> TYPE: DNA
<213> ORGANISM: Artificial Sequence
<220> FEATURE:
<223> OTHER INFORMATION: CDH1 primer set 1 - primer 2

<400> SEQUENCE: 20
cgaaactaac gacccgccc                                                  19
```

```
<210> SEQ ID NO 21
<211> LENGTH: 29
<212> TYPE: DNA
<213> ORGANISM: Artificial Sequence
<220> FEATURE:
<223> OTHER INFORMATION: CDH1 primer set 1 - blocking primer

<400> SEQUENCE: 21
caaaactaac aacccaccca cccaacctc                                    29

<210> SEQ ID NO 22
<211> LENGTH: 27
<212> TYPE: DNA
<213> ORGANISM: Artificial Sequence
<220> FEATURE:
<223> OTHER INFORMATION: CDH1 primer set 1 - probe

<400> SEQUENCE: 22
cccgacctcg cataaacgcg ataaccc                                      27

<210> SEQ ID NO 23
<211> LENGTH: 18
<212> TYPE: DNA
<213> ORGANISM: Artificial Sequence
<220> FEATURE:
<223> OTHER INFORMATION: CDH1 primer set 2 - primer 1

<400> SEQUENCE: 23
ttggggaggg gttcgcgt                                                18

<210> SEQ ID NO 24
<211> LENGTH: 25
<212> TYPE: DNA
<213> ORGANISM: Artificial Sequence
<220> FEATURE:
<223> OTHER INFORMATION: CDH1 primer set 2 - primer 2

<400> SEQUENCE: 24
cgacgccact aaaaaaaaat acgta                                        25

<210> SEQ ID NO 25
<211> LENGTH: 27
<212> TYPE: DNA
<213> ORGANISM: Artificial Sequence
<220> FEATURE:
<223> OTHER INFORMATION: CDH1 primer set 2 - blocking primer

<400> SEQUENCE: 25
gaggggtttg tgttgttgat tggttgt                                      27

<210> SEQ ID NO 26
<211> LENGTH: 31
<212> TYPE: DNA
<213> ORGANISM: Artificial Sequence
<220> FEATURE:
<223> OTHER INFORMATION: CDH1 primer set 2 - probe

<400> SEQUENCE: 26
ttaactaaaa attcacctac cgaccacaac c                                 31

<210> SEQ ID NO 27
<211> LENGTH: 17
<212> TYPE: DNA
<213> ORGANISM: Artificial Sequence
<220> FEATURE:
<223> OTHER INFORMATION: DCLK1 primer set 1 - primer 1
```

```
<400> SEQUENCE: 27
tgcggtggga agagggc                                                  17

<210> SEQ ID NO 28
<211> LENGTH: 17
<212> TYPE: DNA
<213> ORGANISM: Artificial Sequence
<220> FEATURE:
<223> OTHER INFORMATION: DCLK1 primer set 1 - primer 2

<400> SEQUENCE: 28
cacgccctcc cgtctcc                                                  17

<210> SEQ ID NO 29
<211> LENGTH: 23
<212> TYPE: DNA
<213> ORGANISM: Artificial Sequence
<220> FEATURE:
<223> OTHER INFORMATION: DCLK1 primer set 1 - blocking primer

<400> SEQUENCE: 29
tggtgggaag agggtgttgg gag                                           23

<210> SEQ ID NO 30
<211> LENGTH: 24
<212> TYPE: DNA
<213> ORGANISM: Artificial Sequence
<220> FEATURE:
<223> OTHER INFORMATION: DCLK1 primer set 1 - probe

<400> SEQUENCE: 30
acccaccacg actacgcccc aaat                                          24

<210> SEQ ID NO 31
<211> LENGTH: 22
<212> TYPE: DNA
<213> ORGANISM: Artificial Sequence
<220> FEATURE:
<223> OTHER INFORMATION: DCLK1 primer set 2 - primer 1

<400> SEQUENCE: 31
tagtttcggt cgcgtttagt tc                                            22

<210> SEQ ID NO 32
<211> LENGTH: 19
<212> TYPE: DNA
<213> ORGANISM: Artificial Sequence
<220> FEATURE:
<223> OTHER INFORMATION: DCLK1 primer set 2 - primer 2

<400> SEQUENCE: 32
tctacgaaat cccccgacc                                                19

<210> SEQ ID NO 33
<211> LENGTH: 34
<212> TYPE: DNA
<213> ORGANISM: Artificial Sequence
<220> FEATURE:
<223> OTHER INFORMATION: DCLK1 primer set 2 - blocking primer

<400> SEQUENCE: 33
ttggttgtgt ttagtttggt gaggatagta ttag                               34

<210> SEQ ID NO 34
```

```
<211> LENGTH: 22
<212> TYPE: DNA
<213> ORGANISM: Artificial Sequence
<220> FEATURE:
<223> OTHER INFORMATION: DCLK1 primer set 2 - probe

<400> SEQUENCE: 34
accgcgctaa aaccgcctc ct                                          22

<210> SEQ ID NO 35
<211> LENGTH: 18
<212> TYPE: DNA
<213> ORGANISM: Artificial Sequence
<220> FEATURE:
<223> OTHER INFORMATION: FOXL2 primer set 1 - primer 1

<400> SEQUENCE: 35
gggtaaacgt aggaagcg                                              18

<210> SEQ ID NO 36
<211> LENGTH: 18
<212> TYPE: DNA
<213> ORGANISM: Artificial Sequence
<220> FEATURE:
<223> OTHER INFORMATION: FOXL2 primer set 1 - primer 2

<400> SEQUENCE: 36
gactactaac ccctctcg                                              18

<210> SEQ ID NO 37
<211> LENGTH: 30
<212> TYPE: DNA
<213> ORGANISM: Artificial Sequence
<220> FEATURE:
<223> OTHER INFORMATION: FOXL2 primer set 1 - blocking primer

<400> SEQUENCE: 37
tgtaggaagt gggttgggtt aattgtgggt                                 30

<210> SEQ ID NO 38
<211> LENGTH: 21
<212> TYPE: DNA
<213> ORGANISM: Artificial Sequence
<220> FEATURE:
<223> OTHER INFORMATION: FOXL2 primer set 1 - probe

<400> SEQUENCE: 38
ccgctaacga cgcctcgatc g                                          21

<210> SEQ ID NO 39
<211> LENGTH: 18
<212> TYPE: DNA
<213> ORGANISM: Artificial Sequence
<220> FEATURE:
<223> OTHER INFORMATION: FOXL2 primer set 2 - primer 1

<400> SEQUENCE: 39
cgggaagatt tcggtttg                                              18

<210> SEQ ID NO 40
<211> LENGTH: 19
<212> TYPE: DNA
<213> ORGANISM: Artificial Sequence
<220> FEATURE:
<223> OTHER INFORMATION: FOXL2 primer set 2 - primer 2

<400> SEQUENCE: 40
``` ccccaaaaacc taaacttac                                              19

<210> SEQ ID NO 41
<211> LENGTH: 33
<212> TYPE: DNA
<213> ORGANISM: Artificial Sequence
<220> FEATURE:
<223> OTHER INFORMATION: FOXL2 primer set 2 - blocking primer

<400> SEQUENCE: 41
ttttggtttg gagcgttttg tgtttttggg ttt                               33

<210> SEQ ID NO 42
<211> LENGTH: 20
<212> TYPE: DNA
<213> ORGANISM: Artificial Sequence
<220> FEATURE:
<223> OTHER INFORMATION: FOXL2 primer set 2 - probe

<400> SEQUENCE: 42
cgccgccaac aaacccgaaa                                              20

<210> SEQ ID NO 43
<211> LENGTH: 19
<212> TYPE: DNA
<213> ORGANISM: Artificial Sequence
<220> FEATURE:
<223> OTHER INFORMATION: FOXL2 primer set 3 - primer 1

<400> SEQUENCE: 43
tagggtgttt tcgattgtc                                               19

<210> SEQ ID NO 44
<211> LENGTH: 19
<212> TYPE: DNA
<213> ORGANISM: Artificial Sequence
<220> FEATURE:
<223> OTHER INFORMATION: FOXL2 primer set 3 - primer 2

<400> SEQUENCE: 44
ccaacgtaaa taatccgaa                                               19

<210> SEQ ID NO 45
<211> LENGTH: 27
<212> TYPE: DNA
<213> ORGANISM: Artificial Sequence
<220> FEATURE:
<223> OTHER INFORMATION: FOXL2 primer set 3 - blocking primer

<400> SEQUENCE: 45
tttgattgtt gggtggtggg tggaagt                                      27

<210> SEQ ID NO 46
<211> LENGTH: 24
<212> TYPE: DNA
<213> ORGANISM: Artificial Sequence
<220> FEATURE:
<223> OTHER INFORMATION: FOXL2 primer set 3 - probe

<400> SEQUENCE: 46
cgcgccgaaa ctctacaacc acta                                         24

<210> SEQ ID NO 47
<211> LENGTH: 23
<212> TYPE: DNA

```
<213> ORGANISM: Artificial Sequence
<220> FEATURE:
<223> OTHER INFORMATION: HOXA9 primer set 1 - primer 1

<400> SEQUENCE: 47
gggttttagt taggagcgta tgt                                             23

<210> SEQ ID NO 48
<211> LENGTH: 20
<212> TYPE: DNA
<213> ORGANISM: Artificial Sequence
<220> FEATURE:
<223> OTHER INFORMATION: HOXA9 primer set 1 - primer 2

<400> SEQUENCE: 48
ccatcaccac cacccctacg                                                 20

<210> SEQ ID NO 49
<211> LENGTH: 34
<212> TYPE: DNA
<213> ORGANISM: Artificial Sequence
<220> FEATURE:
<223> OTHER INFORMATION: HOXA9 primer set 1 - blocking primer

<400> SEQUENCE: 49
gagtgtatgt atttgttgtt tggtgttgtt gttg                                 34

<210> SEQ ID NO 50
<211> LENGTH: 23
<212> TYPE: DNA
<213> ORGANISM: Artificial Sequence
<220> FEATURE:
<223> OTHER INFORMATION: HOXA9 primer set 1 - probe

<400> SEQUENCE: 50
cgcccgtaac gacgacgacg ccg                                             23

<210> SEQ ID NO 51
<211> LENGTH: 18
<212> TYPE: DNA
<213> ORGANISM: Artificial Sequence
<220> FEATURE:
<223> OTHER INFORMATION: HOXA9 primer set 2 - primer 1

<400> SEQUENCE: 51
gatggtggtg gtatatcg                                                   18

<210> SEQ ID NO 52
<211> LENGTH: 18
<212> TYPE: DNA
<213> ORGANISM: Artificial Sequence
<220> FEATURE:
<223> OTHER INFORMATION: HOXA9 primer set 2 - primer 2

<400> SEQUENCE: 52
acgatattta acgcctcg                                                   18

<210> SEQ ID NO 53
<211> LENGTH: 25
<212> TYPE: DNA
<213> ORGANISM: Artificial Sequence
<220> FEATURE:
<223> OTHER INFORMATION: HOXA9 primer set 2 - blocking primer

<400> SEQUENCE: 53
gtggtatatt gtagtgggta tagtg                                           25
```

<210> SEQ ID NO 54
<211> LENGTH: 21
<212> TYPE: DNA
<213> ORGANISM: Artificial Sequence
<220> FEATURE:
<223> OTHER INFORMATION: HOXA9 primer set 2 - probe

<400> SEQUENCE: 54
cgcgacgaac gccaacgcta t    21

<210> SEQ ID NO 55
<211> LENGTH: 25
<212> TYPE: DNA
<213> ORGANISM: Artificial Sequence
<220> FEATURE:
<223> OTHER INFORMATION: PTGER4 primer set 1 - primer 1

<400> SEQUENCE: 55
ttagatattt ggtgttttat cgatt    25

<210> SEQ ID NO 56
<211> LENGTH: 22
<212> TYPE: DNA
<213> ORGANISM: Artificial Sequence
<220> FEATURE:
<223> OTHER INFORMATION: PTGER4 primer set 1 - primer 2

<400> SEQUENCE: 56
aaaaactaaa acccgcgtac at    22

<210> SEQ ID NO 57
<211> LENGTH: 38
<212> TYPE: DNA
<213> ORGANISM: Artificial Sequence
<220> FEATURE:
<223> OTHER INFORMATION: PTGER4 primer set 1 - blocking primer

<400> SEQUENCE: 57
ttttattgat tggattatta atgtgatggt gtatgttg    38

<210> SEQ ID NO 58
<211> LENGTH: 28
<212> TYPE: DNA
<213> ORGANISM: Artificial Sequence
<220> FEATURE:
<223> OTHER INFORMATION: PTGER4 primer set 1 - probe

<400> SEQUENCE: 58
ataaacgacg tacgccgtca cgttaata    28

<210> SEQ ID NO 59
<211> LENGTH: 24
<212> TYPE: DNA
<213> ORGANISM: Artificial Sequence
<220> FEATURE:
<223> OTHER INFORMATION: PTGER4 primer set 2 - primer 1

<400> SEQUENCE: 59
tgggtattgt agtcgcgagt tatc    24

<210> SEQ ID NO 60
<211> LENGTH: 22
<212> TYPE: DNA
<213> ORGANISM: Artificial Sequence
<220> FEATURE:

<223> OTHER INFORMATION: PTGER4 primer set 2 - primer 2

<400> SEQUENCE: 60
ctacgtaaac aaacgattaa cg                                        22

<210> SEQ ID NO 61
<211> LENGTH: 32
<212> TYPE: DNA
<213> ORGANISM: Artificial Sequence
<220> FEATURE:
<223> OTHER INFORMATION: PTGER4 primer set 2 - blocking primer

<400> SEQUENCE: 61
tgtgagttat tgagatttat gttgggtagt gt                             32

<210> SEQ ID NO 62
<211> LENGTH: 35
<212> TYPE: DNA
<213> ORGANISM: Artificial Sequence
<220> FEATURE:
<223> OTHER INFORMATION: PTGER4 primer set 2 - probe

<400> SEQUENCE: 62
caatctatac gtccaacgta ctcttttacg cgcta                          35

<210> SEQ ID NO 63
<211> LENGTH: 25
<212> TYPE: DNA
<213> ORGANISM: Artificial Sequence
<220> FEATURE:
<223> OTHER INFORMATION: RARB primer set 1 - primer 1

<400> SEQUENCE: 63
gcgtatagag gaatttaaag tgtgg                                     25

<210> SEQ ID NO 64
<211> LENGTH: 27
<212> TYPE: DNA
<213> ORGANISM: Artificial Sequence
<220> FEATURE:
<223> OTHER INFORMATION: RARB primer set 1 - primer 2

<400> SEQUENCE: 64
acgccttttt atttacgacg acttaac                                   27

<210> SEQ ID NO 65
<211> LENGTH: 39
<212> TYPE: DNA
<213> ORGANISM: Artificial Sequence
<220> FEATURE:
<223> OTHER INFORMATION: RARB primer set 1 - blocking primer

<400> SEQUENCE: 65
ttatttacaa caacttaact taaaaaacaa tattccacc                      39

<210> SEQ ID NO 66
<211> LENGTH: 21
<212> TYPE: DNA
<213> ORGANISM: Artificial Sequence
<220> FEATURE:
<223> OTHER INFORMATION: RARB primer set 1 - probe

<400> SEQUENCE: 66
tattccgcct acgcccgctc g                                         21

```
<210> SEQ ID NO 67
<211> LENGTH: 27
<212> TYPE: DNA
<213> ORGANISM: Artificial Sequence
<220> FEATURE:
<223> OTHER INFORMATION: RARB primer set 2 - primer 1

<400> SEQUENCE: 67
gaattttttt atgcgagttg tttgagg                                       27

<210> SEQ ID NO 68
<211> LENGTH: 25
<212> TYPE: DNA
<213> ORGANISM: Artificial Sequence
<220> FEATURE:
<223> OTHER INFORMATION: RARB primer set 2 - primer 2

<400> SEQUENCE: 68
ttccgaatac gttccgaatc ctacc                                         25

<210> SEQ ID NO 69
<211> LENGTH: 33
<212> TYPE: DNA
<213> ORGANISM: Artificial Sequence
<220> FEATURE:
<223> OTHER INFORMATION: RARB primer set 2 - blocking primer

<400> SEQUENCE: 69
ttatgtgagt tgtttgagga ttgggatgtt gag                                33

<210> SEQ ID NO 70
<211> LENGTH: 26
<212> TYPE: DNA
<213> ORGANISM: Artificial Sequence
<220> FEATURE:
<223> OTHER INFORMATION: RARB primer set 2 - probe

<400> SEQUENCE: 70
aacaaaccct actcgaatcg ctcgcg                                        26

<210> SEQ ID NO 71
<211> LENGTH: 21
<212> TYPE: DNA
<213> ORGANISM: Artificial Sequence
<220> FEATURE:
<223> OTHER INFORMATION: RARB primer set 3 - primer 1

<400> SEQUENCE: 71 tgggaattt tcgtttcggt t                                              21

<210> SEQ ID NO 72
<211> LENGTH: 29
<212> TYPE: DNA
<213> ORGANISM: Artificial Sequence
<220> FEATURE:
<223> OTHER INFORMATION: RARB primer set 3 - primer 2

<400> SEQUENCE: 72
acacgtaaac tattaatctt tttcccaac                                     29

<210> SEQ ID NO 73
<211> LENGTH: 34
<212> TYPE: DNA
<213> ORGANISM: Artificial Sequence
<220> FEATURE:
<223> OTHER INFORMATION: RARB primer set 3 - blocking primer
```

```
<400> SEQUENCE: 73
cataaactat taatcttttt cccaacccca aatc                                34

<210> SEQ ID NO 74
<211> LENGTH: 30
<212> TYPE: DNA
<213> ORGANISM: Artificial Sequence
<220> FEATURE:
<223> OTHER INFORMATION: RARB primer set 3 - probe

<400> SEQUENCE: 74
tcatttacca ttttccaaac ttactcgacc                                     30

<210> SEQ ID NO 75
<211> LENGTH: 19
<212> TYPE: DNA
<213> ORGANISM: Artificial Sequence
<220> FEATURE:
<223> OTHER INFORMATION: RASSF1A primer set 1 - primer 1

<400> SEQUENCE: 75
gcgttgaagt cggggttcg                                                 19

<210> SEQ ID NO 76
<211> LENGTH: 19
<212> TYPE: DNA
<213> ORGANISM: Artificial Sequence
<220> FEATURE:
<223> OTHER INFORMATION: RASSF1A primer set 1 - primer 2

<400> SEQUENCE: 76
ccgattaaac ccgtacttc                                                 19

<210> SEQ ID NO 77
<211> LENGTH: 33
<212> TYPE: DNA
<213> ORGANISM: Artificial Sequence
<220> FEATURE:
<223> OTHER INFORMATION: RASSF1A primer set 1 - blocking primer

<400> SEQUENCE: 77
ttggggtttg ttttgtggtt tcgtttggtt tgt                                 33

<210> SEQ ID NO 78
<211> LENGTH: 20
<212> TYPE: DNA
<213> ORGANISM: Artificial Sequence
<220> FEATURE:
<223> OTHER INFORMATION: RASSF1A primer set 1 - probe

<400> SEQUENCE: 78
cgctaacaaa cgcgaaccga                                                20

<210> SEQ ID NO 79
<211> LENGTH: 19
<212> TYPE: DNA
<213> ORGANISM: Artificial Sequence
<220> FEATURE:
<223> OTHER INFORMATION: RASSF1A primer set 2 - primer 1

<400> SEQUENCE: 79
gggagtttga gtttattga                                                 19

<210> SEQ ID NO 80
<211> LENGTH: 21
```

<210> SEQ ID NO 80
<211> LENGTH: 21
<212> TYPE: DNA
<213> ORGANISM: Artificial Sequence
<220> FEATURE:
<223> OTHER INFORMATION: RASSF1A primer set 2 - primer 2

<400> SEQUENCE: 80
gatacgcaac gcgttaacac g                                         21

<210> SEQ ID NO 81
<211> LENGTH: 33
<212> TYPE: DNA
<213> ORGANISM: Artificial Sequence
<220> FEATURE:
<223> OTHER INFORMATION: RASSF1A primer set 2 - blocking primer

<400> SEQUENCE: 81
cacattaaca cactccaacc aaatacaacc ctt                             33

<210> SEQ ID NO 82
<211> LENGTH: 21
<212> TYPE: DNA
<213> ORGANISM: Artificial Sequence
<220> FEATURE:
<223> OTHER INFORMATION: RASSF1A primer set 2 - probe

<400> SEQUENCE: 82
cgcccaacga ataccaactc c                                          21

<210> SEQ ID NO 83
<211> LENGTH: 20
<212> TYPE: DNA
<213> ORGANISM: Artificial Sequence
<220> FEATURE:
<223> OTHER INFORMATION: Septin9 primer set 1 - primer 1

<400> SEQUENCE: 83
cgcgattcgt tgtttattag                                            20

<210> SEQ ID NO 84
<211> LENGTH: 18
<212> TYPE: DNA
<213> ORGANISM: Artificial Sequence
<220> FEATURE:
<223> OTHER INFORMATION: Septin9 primer set 1 - primer 2

<400> SEQUENCE: 84
caccttcgaa atccgaaa                                              18

<210> SEQ ID NO 85
<211> LENGTH: 36
<212> TYPE: DNA
<213> ORGANISM: Artificial Sequence
<220> FEATURE:
<223> OTHER INFORMATION: Septin9 primer set 1 - blocking primer

<400> SEQUENCE: 85
aaaatccaaa ataatcccat ccaactacac attaac                          36

<210> SEQ ID NO 86
<211> LENGTH: 27
<212> TYPE: DNA
<213> ORGANISM: Artificial Sequence
<220> FEATURE:
<223> OTHER INFORMATION: Septin9 primer set 1 - probe

<400> SEQUENCE: 86

```
cgcgttaacc gcgaaatccg acataat                                      27
```

<210> SEQ ID NO 87
<211> LENGTH: 19
<212> TYPE: DNA
<213> ORGANISM: Artificial Sequence
<220> FEATURE:
<223> OTHER INFORMATION: Septin9 primer set 2 - primer 1

<400> SEQUENCE: 87

```
tagcgtattt tcgtttcgc                                               19
```

<210> SEQ ID NO 88
<211> LENGTH: 25
<212> TYPE: DNA
<213> ORGANISM: Artificial Sequence
<220> FEATURE:
<223> OTHER INFORMATION: Septin9 primer set 2 - primer 2

<400> SEQUENCE: 88

```
cgaacttcga aaataaatac taaac                                        25
```

<210> SEQ ID NO 89
<211> LENGTH: 32
<212> TYPE: DNA
<213> ORGANISM: Artificial Sequence
<220> FEATURE:
<223> OTHER INFORMATION: Septin9 primer set 2 - blocking primer

<400> SEQUENCE: 89

```
tttgttttgt gttaggttta tttgtagggt tt                                32
```

<210> SEQ ID NO 90
<211> LENGTH: 22
<212> TYPE: DNA
<213> ORGANISM: Artificial Sequence
<220> FEATURE:
<223> OTHER INFORMATION: Septin9 primer set 2 - probe

<400> SEQUENCE: 90

```
aactactacg accgcgaacg ta                                           22
```

<210> SEQ ID NO 91
<211> LENGTH: 18
<212> TYPE: DNA
<213> ORGANISM: Artificial Sequence
<220> FEATURE:
<223> OTHER INFORMATION: SHOX2 primer set 1 - primer 1

<400> SEQUENCE: 91

```
gttcgtgcga tttcggtc                                                18
```

<210> SEQ ID NO 92
<211> LENGTH: 19
<212> TYPE: DNA
<213> ORGANISM: Artificial Sequence
<220> FEATURE:
<223> OTHER INFORMATION: SHOX2 primer set 1 - primer 2

<400> SEQUENCE: 92

```
tcgctacccc taaactcga                                               19
```

<210> SEQ ID NO 93
<211> LENGTH: 25
<212> TYPE: DNA
<213> ORGANISM: Artificial Sequence

```
<220> FEATURE:
<223> OTHER INFORMATION: SHOX2 primer set 1 - blocking primer

<400> SEQUENCE: 93
tgattttggt tgggtaggtg ggatg                                          25

<210> SEQ ID NO 94
<211> LENGTH: 23
<212> TYPE: DNA
<213> ORGANISM: Artificial Sequence
<220> FEATURE:
<223> OTHER INFORMATION: SHOX2 primer set 1 - probe

<400> SEQUENCE: 94
caaccaaata atctccgtcc cgc                                            23

<210> SEQ ID NO 95
<211> LENGTH: 17
<212> TYPE: DNA
<213> ORGANISM: Artificial Sequence
<220> FEATURE:
<223> OTHER INFORMATION: SHOX2 primer set 2 - primer 1

<400> SEQUENCE: 95
ggcgggcgaa agtaatc                                                   17

<210> SEQ ID NO 96
<211> LENGTH: 20
<212> TYPE: DNA
<213> ORGANISM: Artificial Sequence
<220> FEATURE:
<223> OTHER INFORMATION: SHOX2 primer set 2 - primer 2

<400> SEQUENCE: 96
cgaaaatcgc gaatattccg                                                20

<210> SEQ ID NO 97
<211> LENGTH: 43
<212> TYPE: DNA
<213> ORGANISM: Artificial Sequence
<220> FEATURE:
<223> OTHER INFORMATION: SHOX2 primer set 2 - blocking primer

<400> SEQUENCE: 97
acaaatattc cacttaaacc tattaatctc tataaattaa aca                      43

<210> SEQ ID NO 98
<211> LENGTH: 27
<212> TYPE: DNA
<213> ORGANISM: Artificial Sequence
<220> FEATURE:
<223> OTHER INFORMATION: SHOX2 primer set 2 - probe

<400> SEQUENCE: 98
aaaatcgaat ctacgtttcc acgaaaa                                        27

<210> SEQ ID NO 99
<211> LENGTH: 23
<212> TYPE: DNA
<213> ORGANISM: Artificial Sequence
<220> FEATURE:
<223> OTHER INFORMATION: internal reference gene ACTB primers and probe
      combination - primer 1

<400> SEQUENCE: 99
gtgatggagg aggtttagta agt                                            23
```

```
<210> SEQ ID NO 100
<211> LENGTH: 23
<212> TYPE: DNA
<213> ORGANISM: Artificial Sequence
<220> FEATURE:
<223> OTHER INFORMATION: internal reference gene ACTB primers and probe
      combination - primer 2

<400> SEQUENCE: 100
ccaataaaac ctactcctcc ctt                                              23

<210> SEQ ID NO 101
<211> LENGTH: 30
<212> TYPE: DNA
<213> ORGANISM: Artificial Sequence
<220> FEATURE:
<223> OTHER INFORMATION: internal reference gene ACTB primers and probe
      combination - probe

<400> SEQUENCE: 101
accaccaccc aacacacaat aacaaacaca                                       30
```

METHOD AND KIT FOR IDENTIFYING LUNG CANCER STATUS

CROSS-REFERENCE TO RELATED APPLICATIONS

This application is a national phase entry under 35 U.S.C. § 371 of International Patent Application PCT/CN2018/073817, filed Jan. 23, 2018, designating the United States of America and published as International Patent Publication WO 2019/144275 A1 on Aug. 1, 2019.

TECHNICAL FIELD

The present disclosure relates to a method and a kit for identifying a lung cancer status in a subject.

BACKGROUND

Lung cancer is a malignant tumor with the highest morbidity and mortality in the world, and is a major disease threatening human life and health. The World Cancer Report released by the World Health Organization's International Agency for Research on Cancer (IARC) in 2014 showed that the global cancer burden was increasing. Among new cases of common cancers in 2012, lung cancer ranked first with about 1.8 million cases, accounting for 13% of the total number of common cancers; among common cancer deaths, lung cancer also ranked first with about 1.6 million cases, accounting for 19.4% of the total number. Among the top ten cancers with high incidence, lung cancer had the highest incidence in men, accounting for 23%, and in women, 14.85%, which was second only to breast cancer, 16.97%. In addition, the mortality rate of lung cancer also ranked first in men and women, with 29.50% in men and 23.89% in women.

The prognosis of lung cancer is poor, and it is mostly found in middle or late stage. If lung cancer can be found in early stage and treated with some effective treatment methods, the mortality rate of it could be greatly reduced. Although a series of progress in diagnosis, surgical treatment and research in lung cancer has achieved in recent years, its five-year survival rate remains at a relatively low level of 16%. The reason for this is that patients are often found late in the course of the disease and thus miss the best opportunity for treatment. Foreign studies have found that patients with stage I non-small cell lung cancer can achieve a 5-year survival rate of 58%-73% after undergoing radical surgery. However, only 15% of patients can be founded early. This indicates that, the improvement of the prognosis of lung cancer mainly lies in the improvement of the efficiency of early diagnosis of lung cancer patients.

At present, the diagnosis of lung cancer mainly depends on imaging, sputum exfoliation cytology, and bronchoscopy biopsy. These diagnostic techniques have not greatly reduced the mortality rate of lung cancer patients. Thus, the way to improve the survival rate of lung cancer patients relies on early diagnosis of lung cancer, and screening and mining valuable biological markers of early lung cancer have become an urgent problem to be solved. The diagnostic accuracy of identifying benign and malignant tumors is only 48% by using some tumor markers, such as CEA (carcinoembryonic antigen). Because imaging technology failed to show good results in the early screening of lung cancer, people began to turn their attention to molecular markers for early diagnosis of lung cancer. Unfortunately, no molecular markers with high sensitivity and specificity have been found so far. In recent years, research on lung cancer epigenetics has made rapid progress, especially DNA methylation. It has been found that many specific tumor-related genes have different degrees of methylation status change in the early stage of lung cancer, which provides an opportunity for the exploration of markers for early diagnosis of lung cancer.

Abnormal DNA methylation of the genome and the occurrence of tumors have always been one of the hotspots in medical research. Cell cycle, DNA repair, angiogenesis, apoptosis, etc. involve the methylation of related genes. The most likely regulatory role of DNA hypermethylation is to suppress the expression of key genes, thereby determining the fate of a cell. For example, the study of abnormal DNA methylation in tumor cells has made many significant advances in various tumors. In mammals, methylation only affects a cytosine in front of a guanine (CpG) on a DNA strand. The methylation distribution of CpG dinucleotides in normal cells is not uniform. About 50% of genes have CpG islands with concentrated distribution of CpGs in the promoter region, with lengths ranging from 0.5 to 2 kb. This region is closely related to gene transcription regulation. In humans, the methylation of CpG islands in certain gene regulatory regions occurs frequently in relevant cancer cell tissues, showing a correlation with the onset, disease progression, prognosis, drug sensitivity, etc. of certain tumors. To date, gene methylation abnormalities have been found in most human tumors. Studies have found that epigenetic coding in cancer cells is disturbed, first of all manifested in the disturbance of DNA methylation level, also known as methylation rearrangement. Since the local hypermethylation of a CpG island in a tumor suppressor gene is earlier than the malignant proliferation of cells, the detection of DNA methylation can be used for the early diagnosis of tumorigenesis. Methylation of cancer-related genes is also an early event of lung cancer, so the methylation status of related genes has become an effective indicator for the risk prediction of early lung cancer. Even so, there is still a lack of means to effectively detect the methylation status of these cancer-related genes and process the detected results.

At present, what is urgently needed in the field of respiratory oncology is a clinical test that mini-invasively evaluates and predicts the presence of lung cancer.

BRIEF SUMMARY

In order to solve the above problems, in one aspect, the present disclosure provides a method for identifying a lung cancer status in a subject, which comprises the following steps: 1) collecting a biological sample from the subject; 2) detecting methylation levels of a biomarker gene in the biological sample, wherein the biomarker gene(s) is/are selected from one or more of the following genes: BCAT1, CDH1, DCLK1, FOXL2, HOXA9, PTGER4, RARB, RASSF1A, Septin9, and SHOX2; and 3) comparing the methylation levels detected in step 2) with normal methylation levels of the corresponding biomarker gene(s) in a population to determine the lung cancer status in the subject.

In some embodiments, the method further comprises performing steps 1) and 2) again after the subject undergoes a medical treatment, and comparing the both obtained detection results of the methylation levels to determine the change of the lung cancer status in the subject.

In some embodiments, step 2) may comprise extracting DNA from the biological sample and treating the extracted DNA with bisulfite, so that unmethylated cytosine residues in the DNA are deaminated, and methylated cytosine residues remain unchanged.

In some preferred embodiments, the bisulfite is sodium bisulfite.

In some preferred embodiments, the biomarker genes are selected from 2 or more of BCAT1, CDH1, DCLK1, FOXL2, HOXA9, PTGER4, RARB, RASSF1A, Septin9, and SHOX2.

In a more preferred embodiment, the biomarker genes are selected from 5 or more of BCAT1, CDH1, DCLK1, FOXL2, HOXA9, PTGER4, RARB, RASSF1A, Septin9, and SHOX2.

In some preferred embodiments, the lung cancer status is lung cancer stage I or stage II, and the biomarker gene(s) is/are BCAT1 and/or CDH1.

In some preferred embodiments, the lung cancer status is an adenocarcinoma, and the biomarker gene(s) is/are BCAT1 and/or CDH1.

In some preferred embodiments, the lung cancer status is a squamous cell carcinoma, and the biomarker gene(s) is/are BCAT1 and/or HOXA9.

In some preferred embodiments, the lung cancer status is a large cell lung cancer, and the biomarker gene(s) is/are DCLK1 and/or RASSF1A.

In some preferred embodiments, the lung cancer status is a small cell lung cancer, and the biomarker gene(s) is/are DCLK1 and/or HOXA9.

In some embodiments, step 2) comprises detecting the methylation level of a target region within the biomarker gene(s), wherein the target region is a nucleotide sequence of at least 15 bases in the biomarker gene(s), or a complementary sequence thereof.

In some embodiments, the detection of the methylation level of the BCAT1 gene in step 2) comprises the use of a primer pair having the sequences as set forth in SEQ ID NOs:11 and 12 or a primer pair having the sequences as set forth in SEQ ID NOs:15 and 16 to carry out a PCR amplification reaction, with the bisulfite-treated BCAT1 gene or a fragment thereof in the biological sample as a template; the detection of the methylation level of the CDH1 gene comprises the use of a primer pair having the sequences as set forth in SEQ ID NOs:19 and 20 or a primer pair having the sequences as set forth in SEQ ID NOs:23 and 24 to carry out a PCR amplification reaction, with the bisulfite-treated CDH1 gene or a fragment thereof in the biological sample as a template; the detection of the methylation level of the DCLK1 gene comprises the use of a primer pair having the sequences as set forth in SEQ ID NOs:27 and 28 or a primer pair having the sequences as set forth in SEQ ID NOs:31 and 32 to carry out a PCR amplification reaction, with the bisulfite-treated DCLK1 gene or a fragment thereof in the biological sample as a template; the detection of the methylation level of the FOXL2 gene comprises the use of a primer pair having the sequences as set forth in SEQ ID NOs:35 and 36, a primer pair having the sequences as set forth in SEQ ID NOs:39 and 40 or a primer pair having the sequences as set forth in SEQ ID NOs:43 and 44 to carry out a PCR amplification reaction, with the bisulfite-treated FOXL2 gene or a fragment thereof in the biological sample as a template; the detection of the methylation level of the HOXA9 gene comprises the use of a primer pair having the sequences as set forth in SEQ ID NOs:47 and 48 or a primer pair having the sequences as set forth in SEQ ID NOs:51 and 52 to carry out a PCR amplification reaction, with the bisulfite-treated HOXA9 gene or a fragment thereof in the biological sample as a template; the detection of the methylation level of the PTGER4 gene comprises the use of a primer pair having the sequences as set forth in SEQ ID NOs:55 and 56 or a primer pair having the sequences as set forth in SEQ ID NOs:59 and 60 to carry out a PCR amplification reaction, with the bisulfite-treated PTGER4 gene or a fragment thereof in the biological sample as a template; the detection of the methylation level of the RARB gene comprises the use of a primer pair having the sequences as set forth in SEQ ID NOs:63 and 64, a primer pair having the sequences as set forth in SEQ ID NOs:67 and 68 or a primer pair having the sequences as set forth in SEQ ID NOs:71 and 72 to carry out a PCR amplification reaction, with the bisulfite-treated RARB gene or a fragment thereof in the biological sample as a template; the detection of the methylation level of the RASSF1A gene comprises the use of a primer pair having the sequences as set forth in SEQ ID NOs:75 and 76 or a primer pair having the sequences as set forth in SEQ ID NOs:79 and 80 to carry out a PCR amplification reaction, with the bisulfite-treated RASSF1A gene or a fragment thereof in the biological sample as a template; the detection of the methylation level of the Septin9 gene comprises the use of a primer pair having the sequences as set forth in SEQ ID NOs:83 and 84 or a primer pair having the sequences as set forth in SEQ ID NOs:87 and 88 to carry out a PCR amplification reaction, with the bisulfite-treated Septin9 gene or a fragment thereof in the biological sample as a template; and the detection of the methylation level of the SHOX2 gene comprises the use of a primer pair having the sequences as set forth in SEQ ID NOs:91 and 92 or a primer pair having the sequences as set forth in SEQ ID NOs:95 and 96 to carry out a PCR amplification reaction, with the bisulfite-treated SHOX2 gene or a fragment thereof in the biological sample as a template.

In some preferred embodiments, the detection of the methylation level of the BCAT1 gene in step 2) comprises the use of a primer pair having the sequences as set forth in SEQ ID NOs:11 and 12 and a blocking primer having the sequence as set forth in SEQ ID NO:13, or a primer pair having the sequences as set forth in SEQ ID NOs:15 and 16 and a blocking primer having the sequence as set forth in SEQ ID NO:17 to carry out a PCR amplification reaction, with the bisulfite-treated BCAT1 gene or a fragment thereof in the biological sample as a template; the detection of the methylation level of the CDH1 gene comprises the use of a primer pair having the sequences as set forth in SEQ ID NOs:19 and 20 and a blocking primer having the sequence as set forth in SEQ ID NO:21, or a primer pair having the sequences as set forth in SEQ ID NOs:23 and 24 and a blocking primer having the sequence as set forth in SEQ ID NO:25 to carry out a PCR amplification reaction, with the bisulfate-treated CDH1 gene or a fragment thereof in the biological sample as a template; the detection of the methylation level of the DCLK1 gene comprises the use of a primer pair having the sequences as set forth in SEQ ID NOs:27 and 28 and a blocking primer having the sequence as set forth in SEQ ID NO:29, or a primer pair having the sequences as set forth in SEQ ID NOs:31 and 32 and a blocking primer having the sequence as set forth in SEQ ID NO:33 to carry out a PCR amplification reaction, with the bisulfite-treated DCLK1 gene or a fragment thereof in the biological sample as a template; the detection of the methylation level of the FOXL2 gene comprises the use of a primer pair having the sequences as set forth in SEQ ID NOs:35 and 36 and a blocking primer having the sequence as set forth in SEQ ID NO:37, a primer pair having the sequences as set forth in SEQ ID NOs:39 and 40 and a blocking primer having the sequence as set forth in SEQ ID NO:41, or a primer pair having the sequences as set forth in SEQ ID NOs:43 and 44 and a blocking primer having the sequence as set forth in SEQ ID NO:45 to carry out a PCR amplification reaction, with the bisulfite-treated FOXL2 gene or a fragment thereof in the biological sample as a template; the detection of the methylation level of the HOXA9 gene comprises the use of a primer pair having the sequences as set forth in SEQ ID NOs:47 and 48 and a blocking primer having the sequence as set forth in SEQ ID NO:49, or a primer pair having the sequences as set forth in SEQ ID NOs:51 and 52 and a blocking primer having the sequence as set forth in SEQ ID NO:53 to carry out a PCR amplification reaction, with the bisulfite-treated HOXA9 gene or a fragment thereof in the biological sample as a template; the detection of the methylation level of the PTGER4 gene comprises the use of a primer pair having the sequences as set forth in SEQ ID NOs:55 and 56 and a blocking primer having the sequence as set forth in SEQ ID NO:57, or a primer pair having the sequences as set forth in SEQ ID NOs:59 and 60 and a blocking primer having the sequence as set forth in SEQ ID NO:61 to carry out a PCR amplification reaction, with the bisulfite-treated PTGER4 gene or a fragment thereof in the biological sample as a template; the detection of the methylation level of the RARB gene comprises the use of a primer pair having the sequences as set forth in SEQ ID NOs:63 and 64 and a blocking primer having the sequence as set forth in SEQ ID NO:65, a primer pair having the sequences as set forth in SEQ ID NOs:67 and 68 and a blocking primer having the sequence as set forth in SEQ ID NO:69, or a primer pair having the sequences as set forth in SEQ ID NOs:71 and 72 and a blocking primer having the sequence as set forth in SEQ ID NO:73 to carry out a PCR amplification reaction, with the bisulfite-treated RARB gene or a fragment thereof in the biological sample as a template; the detection of the methylation level of the RASSF1A gene comprises the use of a primer pair having the sequences as set forth in SEQ ID NOs:75 and 76 and a blocking primer having the sequence as set forth in SEQ ID NO:77, or a primer pair having the sequences as set forth in SEQ ID NOs:79 and 80 and a blocking primer having the sequence as set forth in SEQ ID NO:81 to carry out a PCR amplification reaction, with the bisulfite-treated RASSF1A gene or a fragment thereof in the biological sample as a template; the detection of the methylation level of the Septin9 gene comprises the use of a primer pair having the sequences as set forth in SEQ ID NOs:83 and 84 and a blocking primer having the sequence as set forth in SEQ ID NO:85, or a primer pair having the sequences as set forth in SEQ ID NOs:87 and 88 and a blocking primer having the sequence as set forth in SEQ ID NO:89 to carry out a PCR amplification reaction, with the bisulfite-treated Septin9 gene or a fragment thereof in the biological sample as a template; and the detection of the methylation level of the SHOX2 gene comprises the use of a primer pair having the sequences as set forth in SEQ ID NOs:91 and 92 and a blocking primer having the sequence as set forth in SEQ ID NO:93, or a primer pair having the sequences as set forth in SEQ ID NOs: 95 and 96 and a blocking primer having the sequence as set forth in SEQ ID NO: 97 to carry out a PCR amplification reaction, with the bisulfite-treated SHOX2 gene or a fragment thereof in the biological sample as a template, wherein the blocking primers have a 3' end modification, which prevents the extension and amplification of a DNA polymerase.

In further preferred embodiments, the detection of the methylation level of the BCAT1 gene in step 2) comprises the use of a primer pair having the sequences as set forth in SEQ ID NOs:11 and 12, a blocking primer having the sequence as set forth in SEQ ID NO:13 and a probe having the sequence as set forth in SEQ ID NO:14; or a primer pair having the sequences as set forth in SEQ ID NOs:15 and 16, a blocking primer having the sequence as set forth in SEQ ID NO:17 and a probe having the sequence as set forth in SEQ ID NO:18 to carry out a PCR amplification reaction, with the bisulfite-treated BCAT1 gene or a fragment thereof in the biological sample as a template; the detection of the methylation level of the CDH1 gene comprises the use of a primer pair having the sequences as set forth in SEQ ID NOs:19 and 20, a blocking primer having the sequence as set forth in SEQ ID NO:21 and a probe having the sequence as set forth in SEQ ID NO:22; or a primer pair having the sequences as set forth in SEQ ID NOs:23 and 24, a blocking primer having the sequence as set forth in SEQ ID NO:25 and a probe having the sequence as set forth in SEQ ID NO:26 to carry out a PCR amplification reaction, with the bisulfite-treated CDH1 gene or a fragment thereof in the biological sample as a template; the detection of the methylation level of the DCLK1 gene comprises the use of a primer pair having the sequences as set forth in SEQ ID NOs:27 and 28, a blocking primer having the sequence as set forth in SEQ ID NO:29 and a probe having the sequence as set forth in SEQ ID NO:30; or a primer pair having the sequences as set forth in SEQ ID NOs:31 and 32, a blocking primer having the sequence as set forth in SEQ ID NO:33 and a probe having the sequence as set forth in SEQ ID NO:34 to carry out a PCR amplification reaction, with the bisulfite-treated DCLK1 gene or a fragment thereof in the biological sample as a template; the detection of the methylation level of the FOXL2 gene comprises the use of a primer pair having the sequences as set forth in SEQ ID NOs:35 and 36, a blocking primer having the sequence as set forth in SEQ ID NO:37 and a probe having the sequence as set forth in SEQ ID NO:38; a primer pair having the sequences as set forth in SEQ ID NOs:39 and 40, a blocking primer having the sequence as set forth in SEQ ID NO:41 and a probe having the sequence as set forth in SEQ ID NO:42; or a primer pair having the sequences as set forth in SEQ ID NOs:43 and 44, a blocking primer having the sequence as set forth in SEQ ID NO:45 and a probe having the sequence as set forth in SEQ ID NO:46 to carry out a PCR amplification reaction, with the bisulfite-treated FOXL2 gene or a fragment thereof in the biological sample as a template; the detection of the methylation level of the HOXA9 gene comprises the use of a primer pair having the sequences as set forth in SEQ ID NOs:47 and 48, a blocking primer having the sequence as set forth in SEQ ID NO:49 and a probe having the sequence as set forth in SEQ ID NO:50; or a primer pair having the sequences as set forth in SEQ ID NOs:51 and 52, a blocking primer having the sequence as set forth in SEQ ID NO:53 and a probe having the sequence as set forth in SEQ ID NO:54 to carry out a PCR amplification reaction, with the bisulfite-treated HOXA9 gene or a fragment thereof in the biological sample as a template; the detection of the methylation level of the PTGER4 gene comprises the use of a primer pair having the sequences as set forth in SEQ ID NOs:55 and 56, a blocking primer having the sequence as set forth in SEQ ID NO:57 and a probe having the sequence as set forth in SEQ ID NO:58; or a primer pair having the sequences as set forth in SEQ ID NOs:59 and 60, a blocking primer having the sequence as set forth in SEQ ID NO:61 and a probe having the sequence as set forth in SEQ ID NO:62 to carry out a PCR amplification reaction, with the bisulfite-treated PTGER4 gene or a fragment thereof in the biological sample as a template; the detection of the methylation level of the RARB gene comprises the use of a primer pair having the sequences as set forth in SEQ ID NOs:63 and 64, a blocking primer having the sequence as set forth in SEQ ID NO:65 and a probe having the sequence as set forth in SEQ ID NO:66; a primer pair having the sequences as set forth in SEQ ID NOs:67 and 68, a blocking primer having the sequence as set forth in SEQ ID NO:69 and a probe having the sequence as set forth in SEQ ID NO:70; or a primer pair having the sequences as set forth in SEQ ID NOs:71 and 72, a blocking primer having the sequence as set forth in SEQ ID NO:73 and a probe having the sequence as set forth in SEQ ID NO:74 to carry out a PCR amplification reaction, with the bisulfite-treated RARB gene or a fragment thereof in the biological sample as a template; the detection of the methylation level of the RASSF1A gene comprises the use of a primer pair having the sequences as set forth in SEQ ID NOs:75 and 76, a blocking primer having the sequence as set forth in SEQ ID NO:77 and a probe having the sequence as set forth in SEQ ID NO:78; or a primer pair having the sequences as set forth in SEQ ID NOs:79 and 80, a blocking primer having the sequence as set forth in SEQ ID NO:81 and a probe having the sequence as set forth in SEQ ID NO:82 to carry out a PCR amplification reaction, with the bisulfite-treated RASSF1A gene or a fragment thereof in the biological sample as a template; the detection of the methylation level of the Septin9 gene comprises the use of a primer pair having the sequences as set forth in SEQ ID NOs:83 and 84, a blocking primer having the sequence as set forth in SEQ ID NO:85 and a probe having the sequence as set forth in SEQ ID NO:86; or a primer pair having the sequences as set forth in SEQ ID NOs:87 and 88, a blocking primer having the sequence as set forth in SEQ ID NO:89 and a probe having the sequence as set forth in SEQ ID NO:90 to carry out a PCR amplification reaction, with the bisulfite-treated Septin9 gene or a fragment thereof in the biological sample as a template; and the detection of the methylation level of the SHOX2 gene comprises the use of a primer pair having the sequences as set forth in SEQ ID NOs:91 and 92, a blocking primer having the sequence as set forth in SEQ ID NO: 93 and a probe having the sequence as set forth in SEQ ID NO:94; or a primer pair having the sequences as set forth in SEQ ID NOs: 95 and 96, a blocking primer having the sequence as set forth in SEQ ID NO:97 and a probe having the sequence as set forth in SEQ ID NO:98 to carry out a PCR amplification reaction, with the bisulfite-treated SHOX2 gene or a fragment thereof in the biological sample as a template, wherein the probes have a fluorescent group at one end and a fluorescence quenching group at the other end.

In some embodiments, step 2) further comprises using a primer pair having the sequences as set forth in SEQ ID NOs:99 and 100 and a probe having the sequence as set forth in SEQ ID NO:101 to carry out a PCR amplification reaction, with a bisulfite-treated ACTB gene or a fragment thereof used as an internal reference gene in the biological sample as a template.

In some embodiments, step 3) comprises determining the lung cancer status in the subject according to the methylation levels of the biomarker gene(s) based on a logistic regression.

In another aspect, the present disclosure provides a kit for identifying a lung cancer status in a subject, which comprises a primer pair for detecting the methylation levels of a biomarker gene in a biological sample from the subject, wherein the primer pair is used to carry out a PCR amplification reaction with a bisulfite-treated biomarker gene or a fragment thereof as a template; and the biomarker gene(s) is/are selected from one or more of the following genes: BCAT1 CDH1, DCLK1, FOXL2, HOXA9, PTGER4, RARB, RASSF1A, Septin9 and SHOX2.

In some preferred embodiments, the biomarker genes are selected from 2 or more of BCAT1, CDH1, DCLK1, FOXL2, HOXA9, PTGER4, RARB, RASSF1A, Septin9, and SHOX2.

In further preferred embodiments, the biomarker genes are selected from 5 or more of BCAT1, CDH1, DCLK1, FOXL2, HOXA9, PTGER4, RARB, RASSF1A, Septin9, and SHOX2.

In some embodiments, the lung cancer status is lung cancer stage I or stage II, and the biomarker gene(s) is/are BCAT1 and/or CDH1. In some embodiments, the lung cancer status is an adenocarcinoma, and the biomarker gene(s) is/are BCAT1 and/or CDH1. In some embodiments, the lung cancer status is a squamous cell carcinoma, and the biomarker gene(s) is/are BCAT1 and/or HOXA9. In some embodiments, the lung cancer status is a large cell lung cancer, and the biomarker gene(s) is/are DCLK1 and/or RASSF1A. In some embodiments, the lung cancer status is a small cell lung cancer, and the biomarker gene(s) is/are DCLK1 and/or HOXA9.

In some embodiments, in the kit, the primer pair used for the detection of the methylation level of BCAT1 has the sequences as set forth in SEQ ID NOs:11 and 12 or has the sequences as set forth in SEQ ID NOs:15 and 16; the primer pair used for the detection of the methylation level of CDH1 has the sequences as set forth in SEQ ID NOs:19 and 20 or has the sequences as set forth in SEQ ID NOs:23 and 24; the primer pair used for the detection of the methylation level of DCLK1 has the sequences as set forth in SEQ ID NOs:27 and 28 or has the sequences as set forth in SEQ ID NOs:31 and 32; the primer pair used for the detection of the methylation level of FOXL2 has the sequences as set forth in SEQ ID NOs:35 and 36, has the sequences as set forth in SEQ ID NOs:39 and 40, or has the sequences as set forth in SEQ ID NOs:43 and 44; the primer pair used for the detection of the methylation level of HOXA9 has the sequences as set forth in SEQ ID NOs:47 and 48 or has the sequences as set forth in SEQ ID NOs:51 and 52; the primer pair used for the detection of the methylation level of PTGER4 has the sequences as set forth in SEQ ID NOs:55 and 56 or has the sequences as set forth in SEQ ID NOs:59 and 60; the primer pair used for the detection of the methylation level of RARB has the sequences as set forth in SEQ ID NOs:63 and 64, has the sequences as set forth in SEQ ID NOs:67 and 68, or has the sequences as set forth in SEQ ID NOs:71 and 72; the primer pair used for the detection of the methylation level of RASSF1A has the sequences as set forth in SEQ ID NOs:75 and 76 or has the sequences as set forth in SEQ ID NOs:79 and 80; the primer pair used for the detection of the methylation level of Septin9 has the sequences as set forth in SEQ ID NOs:83 and 84 or has the sequences as set forth in SEQ ID NOs:87 and 88; and the primer pair used for the detection of the methylation level of SHOX2 has the sequences as set forth in SEQ ID NOs:91 and 92 or has the sequences as set forth in SEQ ID NOs:95 and 96.

In preferred embodiments, the kit may further comprises a blocking primer, wherein the blocking primer used in combination with the primer pair having the sequences as set forth in SEQ ID NO:11 and 12 has the sequence as set forth in SEQ ID NO:13; the blocking primer used in combination with the primer pair having the sequences as set forth in SEQ ID NO:15 and 16 has the sequence as set forth in SEQ ID NO:17; the blocking primer used in combination with the primer pair having the sequences as set forth in SEQ ID NO:19 and 20 has the sequence as set forth in SEQ ID NO:21; the blocking primer used in combination with the primer pair having the sequences as set forth in SEQ ID NO:23 and 24 has the sequence as set forth in SEQ ID NO:25; the blocking primer used in combination with the primer pair having the sequences as set forth in SEQ ID NO:27 and 28 has the sequence as set forth in SEQ ID NO:29; the blocking primer used in combination with the primer pair having the sequences as set forth in SEQ ID NO:31 and 32 has the sequence as set forth in SEQ ID NO:33; the blocking primer used in combination with the primer pair having the sequences as set forth in SEQ ID NO:35 and 36 has the sequence as set forth in SEQ ID NO:37; the blocking primer used in combination with the primer pair having the sequences as set forth in SEQ ID NO:39 and 40 has the sequence as set forth in SEQ ID NO:41; the blocking primer used in combination with the primer pair having the sequences as set forth in SEQ ID NO:43 and 44 has the sequence as set forth in SEQ ID NO:45; the blocking primer used in combination with the primer pair having the sequences as set forth in SEQ ID NO:47 and 48 has the sequence as set forth in SEQ ID NO:49; the blocking primer used in combination with the primer pair having the sequences as set forth in SEQ ID NO:51 and 52 has the sequence as set forth in SEQ ID NO:53; the blocking primer used in combination with the primer pair having the sequences as set forth in SEQ ID NO:55 and 56 has the sequence as set forth in SEQ ID NO:57; the blocking primer used in combination with the primer pair having the sequences as set forth in SEQ ID NO:59 and 60 has the sequence as set forth in SEQ ID NO:61; the blocking primer used in combination with the primer pair having the sequences as set forth in SEQ ID NO:63 and 64 has the sequence as set forth in SEQ ID NO:65; the blocking primer used in combination with the primer pair having the sequences as set forth in SEQ ID NO:67 and 68 has the sequence as set forth in SEQ ID NO:69; the blocking primer used in combination with the primer pair having the sequences as set forth in SEQ ID NO:71 and 72 has the sequence as set forth in SEQ ID NO:73; the blocking primer used in combination with the primer pair having the sequences as set forth in SEQ ID NO:75 and 76 has the sequence as set forth in SEQ ID NO:77; the blocking primer used in combination with the primer pair having the sequences as set forth in SEQ ID NO:79 and 80 has the sequence as set forth in SEQ ID NO:81; the blocking primer used in combination with the primer pair having the sequences as set forth in SEQ ID NO:83 and 84 has the sequence as set forth in SEQ ID NO:85; the blocking primer used in combination with the primer pair having the sequences as set forth in SEQ ID NO:87 and 88 has the sequence as set forth in SEQ ID NO:89; the blocking primer used in combination with the primer pair having the sequences as set forth in SEQ ID NO:91 and 92 has the sequence as set forth in SEQ ID NO:93; and the blocking primer used in combination with the primer pair having the sequences as set forth in SEQ ID NO:95 and 96 has the sequence as set forth in SEQ ID NO:97, wherein the blocking primers have a 3' end modification, which prevents the extension and amplification of a DNA polymerase.

In preferred embodiments, the kit may further comprises a probe, wherein the probe used in combination with the primer pair having the sequences as set forth in SEQ ID NO:11 and 12 has the sequence as set forth in SEQ ID NO:14; the probe used in combination with the primer pair having the sequences as set forth in SEQ ID NO:15 and 16 has the sequence as set forth in SEQ ID NO:18; the probe used in combination with the primer pair having the sequences as set forth in SEQ ID NO:19 and 20 has the sequence as set forth in SEQ ID NO:22; the probe used in combination with the primer pair having the sequences as set forth in SEQ ID NO:23 and 24 has the sequence as set forth in SEQ ID NO:26; the probe used in combination with the primer pair having the sequences as set forth in SEQ ID NO:27 and 28 has the sequence as set forth in SEQ ID NO:30; the probe used in combination with the primer pair having the sequences as set forth in SEQ ID NO:31 and 32 has the sequence as set forth in SEQ ID NO:34; the probe used in combination with the primer pair having the sequences as set forth in SEQ ID NO:35 and 36 has the sequence as set forth in SEQ ID NO:38; the probe used in combination with the primer pair having the sequences as set forth in SEQ ID NO:39 and 40 has the sequence as set forth in SEQ ID NO:42; the probe used in combination with the primer pair having the sequences as set forth in SEQ ID NO:43 and 44 has the sequence as set forth in SEQ ID NO:46; the probe used in combination with the primer pair having the sequences as set forth in SEQ ID NO:47 and 48 has the sequence as set forth in SEQ ID NO:50; the probe used in combination with the primer pair having the sequences as set forth in SEQ ID NO:51 and 52 has the sequence as set forth in SEQ ID NO:54; the probe used in combination with the primer pair having the sequences as set forth in SEQ ID NO:55 and 56 has the sequence as set forth in SEQ ID NO:58; the probe used in combination with the primer pair having the sequences as set forth in SEQ ID NO:59 and 60 has the sequence as set forth in SEQ ID NO:62; the probe used in combination with the primer pair having the sequences as set forth in SEQ ID NO:63 and 64 has the sequence as set forth in SEQ ID NO:66; the probe used in combination with the primer pair having the sequences as set forth in SEQ ID NO:67 and 68 has the sequence as set forth in SEQ ID NO:70; the probe used in combination with the primer pair having the sequences as set forth in SEQ ID NO:71 and 72 has the sequence as set forth in SEQ ID NO:74; the probe used in combination with the primer pair having the sequences as set forth in SEQ ID NO:75 and 76 has the sequence as set forth in SEQ ID NO:78; the probe used in combination with the primer pair having the sequences as set forth in SEQ ID NO:79 and 80 has the sequence as set forth in SEQ ID NO:82; the probe used in combination with the primer pair having the sequences as set forth in SEQ ID NO:83 and 84 has the sequence as set forth in SEQ ID NO:86; the probe used in combination with the primer pair having the sequences as set forth in SEQ ID NO:87 and 88 has the sequence as set forth in SEQ ID NO:90; the probe used in combination with the primer pair having the sequences as set forth in SEQ ID NO:91 and 92 has the sequence as set forth in SEQ ID NO:94; and the probe used in combination with the primer pair having the sequences as set forth in SEQ ID NO:95 and 96 has the sequence as set forth in SEQ ID NO:98, wherein the probes have a fluorescent group at one end and a fluorescence quenching group at the other end.

In further preferred embodiments, the kit comprises the primer pair and the corresponding blocking primer and probe.

In some embodiments, the kit further comprises a primer pair having the sequences as set forth in SEQ ID NOs:99 and 100 and a probe having the sequence as set forth in SEQ ID NO:101, for carrying out a PCR amplification reaction, with a bisulfite-treated ACTB gene or a fragment thereof used as an internal reference gene in the biological sample as a template.

In preferred embodiments, the kit further comprises a DNA extraction reagent and a bisulfite reagent. Preferably, the bisulfite reagent comprises sodium bisulfite.

In preferred embodiments, the kit further comprises an instruction that describes how to use the kit and process detection results with a logistic regression.

The lung cancer status includes the lung cancer susceptibility and the presence, progression, subtype, and/or stage of the lung cancer.

The biological sample is selected from blood, serum, plasma, sputum, lymph, cerebrospinal fluid, pleural fluid, bronchoalveolar lavage fluid, urine, and tissue biopsy from the subject.

The method and kit provided by the present disclosure provide a fast, reliable, and accurate new way for the prediction, diagnosis, and evaluation of a lung cancer.

BRIEF DESCRIPTION OF THE DRAWINGS

FIG. 2A shows the methylation level distribution of BCAT1, CDH1, DCLK1, FOXL2, HOXA9 and PTGER4, and FIG. 2B shows the methylation level distribution of RARB, RASSF1A, Septin9 and SHOX2.

FIG. 3A shows the methylation level distribution of BCAT1, CDH1, DCLK1, FOXL2, HOXA9 and TGER4, and FIG. 2B shows the methylation level distribution of RARB, RASSF1A, Septin9 and SHOX2.

DETAILED DESCRIPTION

Figure 1:
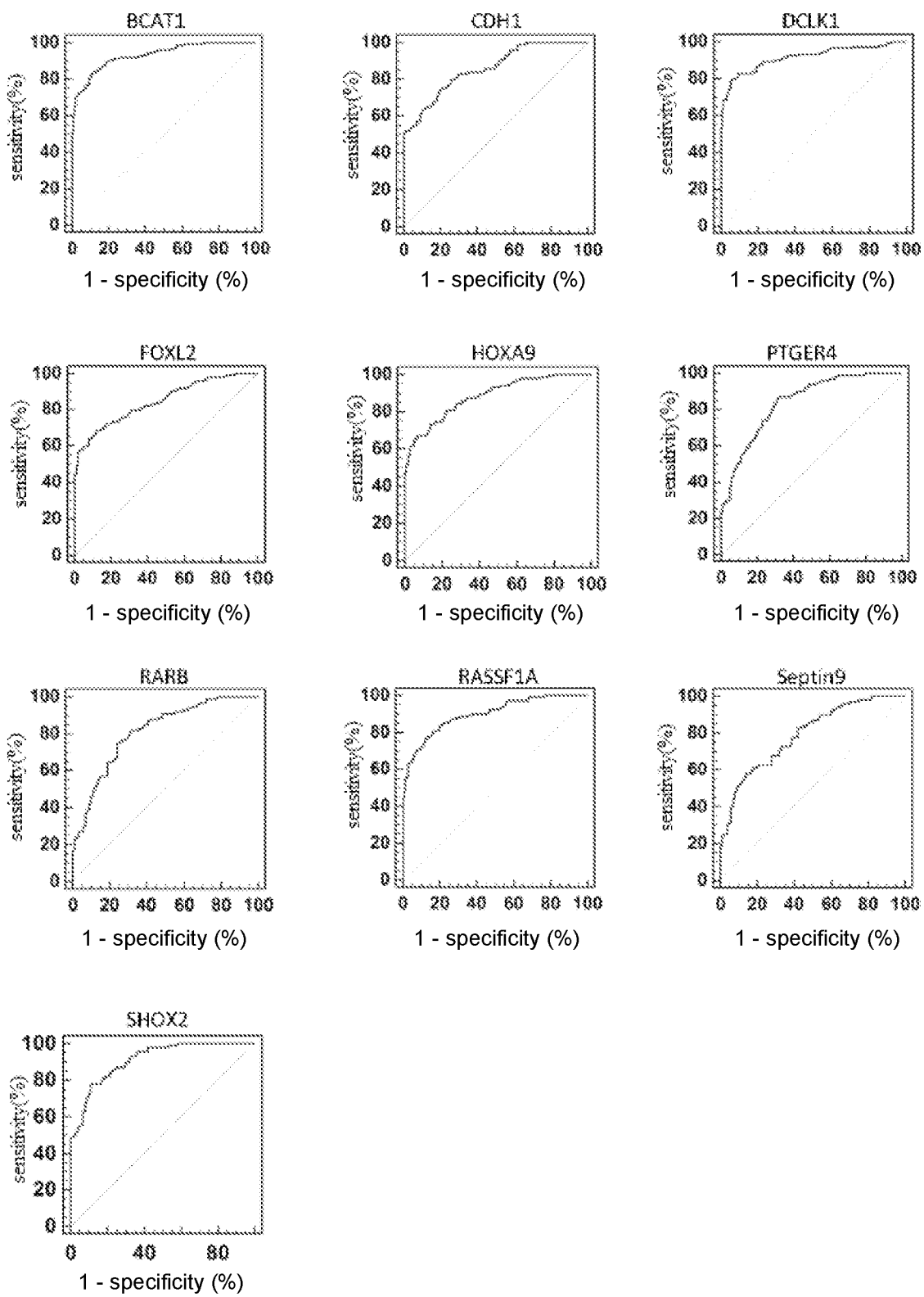
FIG. 1 shows the receiver operating characteristic (ROC) curves of the methylation levels of 10 biomarker genes.

Unless otherwise described, the technical terms used in this disclosure have the meanings generally understood by those skilled in the art to which the present disclosure belongs.

The present disclosure in one aspect relates to a method for identifying a lung cancer status in a subject, which comprises the following steps: 1) collecting a biological sample from the subject; 2) detecting the methylation levels of a biomarker gene in the biological sample, wherein the biomarker gene(s) is/are selected from one or more of the following genes: BCAT1 (Branched Chain Amino acid Transaminase 1), CDH1 (Cadherin 1), DCLK1 (Doublecortin Like Kinase 1), FOXL2 (Forkhead Box L2), HOXA9 (Homeobox A9), PTGER4 (Prostaglandin E Receptor 4), RARB (Retinoic Acid Receptor Beta), RASSF1A (Ras association domain family 1A), Septin9 and SHOX2 (Short stature homeobox 2); and 3) comparing the methylation levels detected in step 2) with the normal methylation levels of the corresponding biomarker gene(s) in a population to determine the lung cancer status in the subject.

The term "subject" as used herein refers to an individual (preferably a human) suffering from or suspected of having a certain disease, or, when predicting the susceptibility, "subject" may also include healthy individuals. The term is generally used interchangeably with "patient," "test subject," "treatment subject," and the like.

The term "population" as used herein generally refers to healthy people. When referring to a specific disease (such as a lung cancer), a "population" may include individuals who do not suffer from the specific disease but may suffer from other diseases. In addition, it is also possible to select only some individuals as the "population" based on characteristics such as, age, gender, health status, smoking or not, etc. A "normal methylation level in a population" can be obtained by detecting enough individuals or can be found in an existing clinical literature. In some cases, this normal level refers to no methylation.

The term "lung cancer status" used herein includes a lung cancer susceptibility and the presence, progression, subtype, and/or stage of a lung cancer. In some embodiments, the subject's susceptibility to a lung cancer can be predicted based on the methylation levels of the biomarker gene(s) in the subject. In other embodiments, the subject may be identified for the presence of a lung cancer based on the methylation levels of the biomarker gene(s) in the subject; and if a lung cancer is present, the subtype and/or the stage of the lung cancer is identified. Lung cancer subtypes may include adenocarcinoma, squamous cell carcinoma, large cell lung cancer, and small cell lung cancer. The lung cancer stages may include stage I (IA, IB, or IC), stage II, stage III, and stage IV. In some embodiments, the lung cancer is a stage I lung cancer. In some embodiments, the lung cancer is a stage II lung cancer. In some embodiments, the lung cancer is a stage III lung cancer. In other embodiments, the lung cancer is a stage IV lung cancer.

In the method of the present disclosure, treatment of the subject, for example, including performing more tests on the subject, performing a surgery, giving medications, and taking no further actions, may also be arranged based on the stage of the lung cancer. In other embodiments, the method of the present disclosure further comprises measuring the methylation levels of one or more biomarker genes of BCAT1, CDH1, DCLK1, FOXL2, HOXA9, PTGER4, RARE, RASSF1A, Septin9, and SHOX2 genes or fragments thereof in the subject after the subject is treated, and correlating the measurement results with the lung cancer status to identify whether the treatment results in a change in the lung cancer status in the subject. In some embodiments, the correlation is performed by a classification algorithm of a software.

The detection of the methylation levels in step 2) comprises extracting DNA from a biological sample, treating it with bisulfite, and then carrying out a PCR amplification by using a methylation-specific primer pair. The bisulfite treatment causes unmethylated cytosine residues in a double-stranded DNA molecule to be deaminated to be uracils; while methylated cytosine residues remain unchanged. As a result, in the subsequent PCR amplification reaction, methylated cytosine residue sites on a template are paired with guanine residues in a primer as cytosine residues, while unmethylated cytosine residue sites are paired with adenine residues in a primer as uracil residues. The inventors designed multiple primer pairs for each biomarker gene to detect the methylation level of the target region within each biomarker gene. The target regions are selected from the fragments of at least 15 consecutive bases in the sequences as set forth in SEQ ID NOs:1-10, respectively; and the nucleic acid sequences of the primer pairs are respectively identical, complementary or hybridizable to the above target regions. The primer pairs provided herein make use of the methylation difference to detect the methylation levels of the target regions within the biomarker genes. When a target region of a biomarker gene is not methylated, the primer pair used cannot effectively pair with and bind to the target region (treated with bisulfite), which is used as a template in the PCR amplification reaction, and cannot (or rarely) generate amplification products; and when the target gene of the biomarker gene is methylated, the primer pair used is able to effectively pair with and bind to the target region (treated with bisulfite), which is used as a template in the PCR amplification reaction, and thus generate amplification products. The differences of these amplification reactions can be monitored in real time during the amplification reactions, or can be judged by detecting the amplification products. After many experiments, the inventors screened out multiple primer pairs for the biomarker genes (see below), which can be used alone or in combination to help identify the lung cancer status in the subject.

The term "biomarker gene or a fragment thereof" is often used herein when referring to the detection of a methylation level, because, in the choice of a template, as long as the length of the template is not less than the length of the region to be amplified, the primer pair used in the PCR amplification reaction does not distinguish between the entire gene or a fragment thereof (in fact, during the DNA extraction and subsequent bisulfite treatment, the gene is usually broken into fragments of different sizes).

In further preferred embodiments, the present disclosure uses the HeavyMethyl method to measure marker gene methylation. Therefore, in addition to the design of common Taqman primers, blocking primers are also designed. The nucleotide sequence of a blocking primer is designed to be paired with and bind to a template sequence in the region amplified by a corresponding primer pair.

In addition, a chemical modification is introduced into a blocking primer at 3'-OH, which prevents the amplification with a DNA polymerase. The chemical modifications are, for example, C3 spacer (C3 Spacer), C6 spacer (C6 Spacer), inverted 3' end, 3' phosphate (3'P), etc. In embodiments of the method of the present disclosure, the nucleotide sequence of a blocking primer is designed to bind to an unmethylated template (treated with sulfite), but not to a methylated template (treated with sulfite). Therefore, when no methylation occurs in the region corresponding to a blocking primer, it can prevent the corresponding amplification reaction, and thereby improving the specificity of the detection method of the present disclosure.

In further preferred embodiments of the method of the present disclosure, it further comprises the use of fluorescent probes to monitor and/or quantify PCR amplification reactions in real time. The fluorescent report group at 5' end of a probe used may be FAM, JOE, TET, HEX, Cy3, Texas Red, Rox, or Cy5; the quenching group at the 3' end is BHQ1, BHQ2, BHQ3, TAMRA, DABCYL, or MGB.

The detection of the methylation levels of the biomarker gene(s) in the method of the present disclosure includes detecting whether there is/are methylation(s) in the biomarker gene, and quantitative and qualitative detection of the methylation(s).

The biological sample is selected from fluids or tissues extracted form the subject, and includes blood, serum, plasma, sputum, lymph, cerebrospinal fluid, pleural fluid, bronchoalveolar lavage fluid, urine, tissue biopsy, etc.

In the method of the present disclosure, the age of the subject and the smoking index SI can also be considered to predict the lung cancer status in the subject.

In some embodiments, the method of the present disclosure further comprises the step of providing a written report or an electronic report on the lung cancer prediction, and optionally, the report comprises a prediction about the presence or not or likelihood of a lung cancer in the subject, or about the risk gradation of a lung cancer in the subject.

In some embodiments, the method of the present disclosure further comprises establishing a report for a physician on the relative methylation levels of biomarker gene(s), and transmitting such report by post, fax, mailbox, etc. In one embodiment, a data stream containing the report of methylation levels of biomarker gene(s) is transmitted through the internet.

In some embodiments, a statistical method is used to construct a diagnostic model based on the methylation levels of the biomarker gene(s). The statistical method is selected from the following methods: multiple linear regression, lookup table, decision tree, support vector machine, Probit regression, Logistic regression, cluster analysis, neighborhood analysis, genetic algorithm, Bayesian and non-Bayesian methods, etc.

In other embodiments, a prediction or diagnostic model based on the methylation levels of the biomarker gene(s) is provided. The model may be in the form of software code, a computer-readable format, or a written description for evaluating the relative methylation levels of the biomarker gene(s).

New and important additional information, which assists the physician in grading the risk of a patient suffering from a lung cancer and planning the diagnostic steps to be taken next, can be obtained by using the method of the present disclosure. The method provided herein can similarly be used to assess the risk of a lung cancer in an asymptomatic high-risk patient, and as a screening tool for the general population. It is contemplated that the method of the present disclosure can be used by a clinician as part of a comprehensive assessment of other predictive and diagnostic indicators.

The method of the present disclosure can be used to evaluate therapeutic efficacies of existing chemotherapeutic agents, candidate chemotherapeutic agents and other types of cancer treatments. For example, biological samples can be taken from a subject before or after a treatment or during a treatment of the subject, and the methylation levels of the biomarker gene(s) can be detected as described above. The detection results are used to identify changes in the cancer status in the subject so as to determine therapeutic efficacy.

The method of the present disclosure can also be used to identify whether a subject is potentially developing a cancer. Relative methylation levels of the biomarker gene(s) in biological samples taken from a subject over time are detected, and the changes in the methylation levels of the biomarkers that point to the characteristics of a cancer are interpreted as a progress toward the cancer.

The combination of the biomarker genes provides a sensitive, specific and accurate means for predicting the presence of a lung cancer or detecting a lung cancer in different stages of the lung cancer progression. Evaluation of the methylation levels in the biological sample may also be correlated with the presence of a pre-malignant or pre-clinical disorder in a patient. Therefore, the disclosed method can be used to predict or detect the presence of a lung cancer in a sample, the stage of a lung cancer, the subtype of a lung cancer, the benignity or malignancy of a lung cancer, the possibility of metastasis of a lung cancer, the histological type of a neoplasm associated with a lung cancer, the painlessness or aggressiveness of a cancer, and other lung cancer characteristics related to the prevention, diagnosis, characterization, and treatment of a lung cancer in a patient.

The method of the present disclosure can also be used to evaluate the effectiveness of a candidate drug to inhibit a lung cancer, evaluate the efficacy of a lung cancer therapy, monitor the progress of a lung cancer, select agents or therapies to inhibit a lung cancer, monitor the treatment of a lung cancer patient, monitor the inhibition status of a lung cancer in a patient, and detect the methylation levels of the biomarker gene(s) in an animal after exposed to a test compound so as to assess the carcinogenic potential of the test compound.

The present disclosure further provides a kit for detecting the lung cancer status. In some embodiments, the kit may include DNA extraction reagents and bisulfite reagents. The DNA extraction reagents may include a lysis buffer, a binding buffer, a washing buffer, and an elution buffer. The lysis buffer is usually composed of a protein denaturant, a detergent, a pH buffering agent and a nuclease inhibitor. The binding buffer is usually composed of a protein denaturant and a pH buffer agent. The washing buffer is divided into washing buffer A and washing buffer B: washing buffer A is composed of a protein denaturant, a nuclease inhibitor, a detergent, a pH buffering agent and ethanol; washing buffer B is composed of a nuclease inhibitor, a pH buffering agent and ethanol. The elution buffer is usually composed of a nuclease inhibitor and a pH buffering agent. The protein denaturant is selected from one or more of guanidine isothiocyanate, guanidine hydrochloride and urea; the detergent is selected from one or more of TWEEN® 20, IGEPAL CA-630, Triton X-100, NP-40 and SDS; the pH buffering agent is selected from one or more of Tris, boric acid, phosphate, MES and HEPES; the nuclease inhibitor is selected from one or more of EDTA, EGTA and DEPC. The bisulfite reagents include a bisulfite buffer and a protective buffer, in which the bisulfite salt is selected from one or more of sodium metabisulphite, sodium sulfite, sodium bisulfite, ammonium bisulfite and ammonium sulfite; the protection buffer is composed of an oxygen radical scavenger, and the oxygen radical scavenger is selected from one or more of hydroquinone, vitamin E, vitamin E derivatives, gallic acid, Trolox, trihydroxybenzoic acid and trihydroxybenzoic acid derivatives.

The kit of the present disclosure comprises a primer pair or primer pairs for methylation-specific PCR amplification reaction(s) for one or more of BCAT1, CDH1, DCLK1, FOXL2, HOXA9, PTGER4, RARB, RASSF1A, Septin9 and SHOX2 gene. These primer pairs respectively detect the methylation of at least one nucleotide sequence in the nucleotide sequence of a target region of the corresponding gene.

The kit of the present disclosure may further comprise blocking primers and probes used in combination with the above-mentioned primer pairs (these blocking primers and probes are described above and below).

In certain embodiments, the kit may further comprise an instruction for using the kit to extract DNA from a biological sample and treating the DNA with a bisulfate reagent. In other embodiments, the kit further comprises an instruction for using the reagents in the kit to measure a biomarker level in the subject. In still other embodiments, the kit comprises an instruction for using the kit to determine the lung cancer status in a subject.

The present disclosure further discloses the method for detecting the methylation levels of the biomarker genes or fragments thereof with the kit. The method comprises the steps: extracting DNA in a biological sample by using the DNA extraction reagents, treating the extracted DNA with the bisulfate reagents, and using the treated DNA as a template to detect the methylation levels of the biomarker genes with the provided primer pairs.

The measurement method for the methylation level of a biomarker gene may be selected from one or more of the following methods: real-time fluorescent PCR, digital PCR, bisulfite sequencing, methylation-specific PCR, restriction enzyme analysis, high-resolution dissolution curve technology, gene chip technology and time-of-flight mass spectrometry.

The present disclosure is further described by the following examples.

Example 1: DNA Extraction

The DNA extraction reagents are composed of a lysis buffer, a binding buffer, a washing buffer, and an elution buffer. The lysis buffer is composed of a protein denaturant, a detergent, a pH buffering agent and a nuclease inhibitor. The binding buffer is composed of a protein denaturant and a pH buffering agent. The washing buffer is divided into washing buffer A and washing buffer B. Washing buffer A is composed of a protein denaturant, a nuclease inhibitor, a detergent, a pH buffering agent and ethanol; washing buffer B is composed of a nuclease inhibitor, a pH buffering agent and ethanol. The elution buffer is composed of a nuclease inhibitor and a pH buffering agent. The protein denaturant is guanidine hydrochloride; the detergent is TWEEN® 20; the pH buffering agent is Tris-HCl; and the nuclease inhibitor is EDTA.

In this example, a plasma sample of a lung cancer patient is taken as an example to extract plasma DNA. The extraction method comprises the following steps:
(1) add to 1 ml of the plasma the same volume of the lysis buffer, then add proteinase K and Carrier RNA to achieve a final concentration of 100 mg/L and 1 μg/ml, mix by shaking, and incubate at 55° C. for 30 minutes;
(2) add 100 μL magnetic beads, then add 2 ml of the binding buffer, and incubate for 1 hour with shaking;
(3) adsorb the magnetic beads with a magnetic separator (purchased from Life technologies, catalog No: 37002D), and discard the supernatant solution;
(4) add 1 ml of the washing buffer A to resuspend the magnetic beads and wash for 1 minute with shaking;
(5) adsorb the magnetic beads with the magnetic separator and discard the supernatant;
(6) add 1 ml of washing buffer B to resuspend the magnetic beads and wash for 1 minute with shaking;
(7) adsorb the magnetic beads with the magnetic separator and discard the supernatant solution;
(8) quickly centrifuge at 10,000 rpm for 1 minute, absorb the magnetic beads with the magnetic separator, and remove the residual supernatant solution;
(9) place the centrifuge tube loaded with the magnetic beads on a 55° C. metal bath, and dry it for 10 minutes, with the lid open;
(10) add 100 μl of the elution buffer to resuspend the magnetic beads, place it on a 65° C. metal bath, and elute for 10 minutes with shaking;
(11) adsorb the magnetic beads with the magnetic separator, take out the buffer containing the target DNA, quantify the DNA, and make a mark;

(12) store the eluted DNA in a refrigerator at 4° C. for later use, or in a refrigerator at −20° C. for long-term storage.

Example 2: Treatment of DNA with Bisulfite

Treatment of DNA with bisulfite is to treat the extracted DNA sample with the bisulfite reagents. The bisulfite reagents are composed of a bisulfite buffer and a protective buffer. The bisulfite buffer is a mixed solution of sodium bisulfite and water; the protective buffer is a mixed solution of oxygen radical scavenger hydroquinone and water.

The DNA extracted in Example 1 is used as the processing object in this Example, and the DNA is treated with bisulfite. The procedure comprises:
(1) prepare the bisulfite buffer: weigh 1 g of sodium bisulfite powder, and add water to it to obtain 3 M buffer solution;
(2) prepare the protective buffer: weigh 1 g of hydroquinone reagent, and add water to it to obtain 0.5 M protective buffer;
(3) mix together 100 μl of the DNA solution, 200 μl of the bisulfite buffer and 50 μl of the protective solution, and mix by shaking;
(4) perform a thermal cycling: 95° C. for 5 minutes, 80° C. for 60 minutes, and 4° C. for 10 minutes;
(5) add 1 ml of the DNA binding buffer to the bisulfite-treated DNA solution, add 50 μl magnetic beads, and incubate for 1 hour with shaking;
(6) adsorb the magnetic beads with a magnetic separator, and discard the supernatant solution;
(7) add 0.5 ml of the washing buffer A to resuspend the magnetic beads and wash for 1 minute with shaking;
(8) adsorb the magnetic beads with the magnetic separator, and discard the supernatant;
(9) add 0.5 ml of the washing buffer B to resuspend the magnetic beads and wash for 1 minute with shaking;
(10) adsorb the magnetic beads with the magnetic separator, and discard the supernatant;
(11) quickly centrifuge at 10,000 rpm for 1 minute, absorb the magnetic beads with the magnetic separator, and remove the residual supernatant solution;
(12) place the centrifuge tube loaded with the magnetic beads on a 55° C. metal bath, and dry it for 10 minutes, with the lid open;
(13) add 50 μl of the elution buffer to resuspend the magnetic beads, place it on a 65° C. metal bath, and elute for 10 minutes with shaking;
(14) adsorb the magnetic beads with the magnetic separator, take out the buffer containing the target DNA, quantify the DNA, and make a mark.

Example 3: Real-Time PCR Detection of DNA Methylation and Verification of Primer Sets In this example, a real-time fluorescent PCR was used as an example to detect the methylation levels of biomarker genes. The genes to be detected were BCAT1, CDH1, DCLK1, FOXL2, HOXA9, PTGER4, BARB, RASSF1A, Septin9 and SHOX2 genes, and the internal reference gene was ACTB. In this example, the bisulfate-treated DNA of Example 2 was used as a template for real-time fluorescent PCR amplification. The DNA samples to be detected, negative quality control products, positive quality control products and no template controls were all detected with three replicates.

For BCAT1, CDH1, DCLK1, FOXL2, HOXA9, PTGER4, RARB, RASSF1A, Septin9 and SHOX2 genes, many sets of primer and probe combinations could be designed. However, the performance of each set of the probe and primer combinations might be different, so they needed to be verified through experiments. In this Example, the primers and probes for BCAT1, CDH1, DCLK1, FOXL2, HOXA9, PTGER4, BARB, RASSF1A, Septin9, and SHOX2 genes were verified using methylated and unmethylated DNA templates.

Therefore, a variety of primers and probes were designed for BCAT1, CDH1, DCLK1, FOXL2, HOXA9, PTGER4, RARB, RASSF1A, Septin9, and SHOX2 genes, which were respectively equivalent to, complementary to, or hybridizable to at least 15 consecutive nucleotides of the sequences as set forth in SEQ ID NOs:1-10 or complementary sequences thereof and verified the effectiveness of the designed primers and probes with methylated and unmethylated nucleic acid sequences as templates. The following optimal primer sets and a primer set were selected for the internal reference gene ACTB through real-time fluorescence PCR amplification results.

```
BCAT1 primer set 1
primer 1: SEQ ID NO 11:
5'-TGTTGATGTAATTCGTTAGGTCGC-3' primer 2: SEQ ID NO 12:
5'-AATACCCGAAACGACGACG-3' blocking primer: SEQ ID NO 13:
5'-ATTTGTTAGGTTGTGAGTTTTTGTTGTGAGAG-C3-3' probe: SEQ ID NO 14:
5'-TEXAS RED-AAACCGACCCTCTCGCGACGAA-BHQ2-3'

BCAT1 primer set 2
primer 1: SEQ ID NO 15:
5'-TTTATTGTTTCGTCGGTTACG-3' primer 2: SEQ ID NO 16:
5'-CCCAAATCTTACTACAACCG-3' blocking primer: SEQ ID NO 17:
5'-TGTTGGTTATGAGGGAAGTTTGAGTTGAGTG-C3-3' probe: SEQ ID NO 18:
5'-TEXAS RED-CGCGCTCTACAACCGCAAACCCG-BHQ2-3'

CDH1 primer set 1
primer 1: SEQ ID NO 19:
5'-CGAATTTAGTGGAATTAGAATCGTG-3' primer 2: SEQ ID NO 20:
5'-CGAAACTAACGACCCGCCC-3' blocking primer: SEQ ID NO 21
5'-CAAAACTAACAACCCACCCACCCAACCTC-C3-3' probe: SEQ ID NO 22:
5'-JOE-CCCGACCTCGCATAAACGCGATAACCC-BHQ1-3'

CDH1 primer set 2
primer 1: SEQ ID NO 23:
5'-TTGGGGAGGGGTTCGCGT-3' primer 2: SEQ ID NO 24:
5'-CGACGCCACTAAAAAAAAATACGTA-3' blocking primer: SEQ ID NO 25
5'-GAGGGGTTTGTGTTGTTGATTGGTTGT-C3-3' probe: SEQ ID NO 26:
5'-JOE-TTAACTAAAAATTCACCTACCGACCACAACC-BHQ1-3'
```

-continued

DCLK1 primer set 1
primer1: SEQ ID NO 27:
5'-TGCGGTGGGAAGAGGGC-3' primer 2: SEQ ID NO 28:
5'-CACGCCCTCCCGTCTCC-3' blocking primer: SEQ ID NO 29:
5'-TGGTGGGAAGAGGGTGTTGGGAG-C3-3' probe: SEQ ID NO 30:
5'-HEX-ACCCACCACGACTACGCCCCAAAT-BHQ1-3'

DCLK1 primer set 2
primer 1: SEQ ID NO 31:
5'-TAGTTTCGGTCGCGTTTAGTTC-3' primer 2: SEQ ID NO 32:
5'-TCTACGAAATCCCCCGACC-3' blocking primer: SEQ ID NO 33:
5'-TTGGTTGTGTTTAGTTTGGTGAGGATAGTATTAG-C3-3' probe: SEQ ID NO 34:
5'-HEX-ACCGCGCTAAAAACCGCCTCCT-BHQ1-3'

FOXL2 primer set 1
primer 1: SEQ ID NO 35:
5'-GGGTAAACGTAGGAAGCG-3' primer 2: SEQ ID NO 36:
5'-GACTACTAACCCCTCTCG-3' blocking primer: SEQ ID NO 37:
5'-TGTAGGAAGTGGGTTGGGTTAATTGTGGGT-3'P-3' probe: SEQ ID NO 38:
5'-FAM-CCGCTAACGACGCCTCGATCG-BHQ1-3'

FOXL2 primer set 2
primer 1: SEQ ID NO 39:
5'-CGGGAAGATTTCGGTTTG-3' primer 2: SEQ ID NO 40:
5'-CCCCAAAACCTAAACTTAC-3' blocking primer: SEQ ID NO 41:
5'-TTTTGGTTTGGAGCGTTTTGTGTTTTTGGGTTT-3'P-3' probe: SEQ ID NO 42:
5'-FAM-CGCCGCCAACAAACCCGAAA-BHQ1-3'

FOXL2 primer set 3
primer 1: SEQ ID NO 43:
5'-TAGGGTGTTTTCGATTGTC-3' primer 2: SEQ ID NO 44:
5'-CCAACGTAAATAATCCGAA-3' blocking primer: SEQ ID NO 45:
5'-TTTGATTGTTGGGTGGTGGGTGGAAGT-3'P-3' probe: SEQ ID NO 46:
5'-FAM-CGCGCCGAAACTCTACAACCACTA-BHQ1-3'

HOXA9 primer set 1
primer 1: SEQ ID NO 47:
5'-GGGTTTTAGTTAGGAGCGTATGT-3' primer 2: SEQ ID NO 48:
5'-CCATCACCACCACCCCTACG-3' blocking primer: SEQ ID NO 49:
5'-GAGTGTATGTATTTGTTGTTTGGTGTTGTTGTTG-C3-3' probe: SEQ ID NO 50:
5'-TEXAS RED-CGCCCGTAACGACGACGACGCCG-BHQ2-3'

HOXA9 primer set 2
primer 1: SEQ ID NO 51:
5'-GATGGTGGTGGTATATCG-3' primer 2: SEQ ID NO 52:
5'-ACGATATTTAACGCCTCG-3' blocking primer: SEQ ID NO 53:
5'-GTGGTATATTGTAGTGGGTATAGTG-C3-3' probe: SEQ ID NO 54:
5'-TEXAS RED CGCGACGAACGCCAACGCTAT-BHQ2-3'

PTGER4 primer set 1
primer 1: SEQ ID NO 55:
5'-TTAGATATTTGGTGTTTTATCGATT-3' primer 2: SEQ ID NO 56:
5'-AAAAACTAAAACCCGCGTACAT-3' blocking primer: SEQ ID NO 57:
5'-TTTTATTGATTGGATTATTAATGTGATGGTGTATGTTG-3'P-3' probe: SEQ ID NO 58:
5'-JOE-ATAAACGACGTACGCCGTCACGTTAATA-BHQ1-3'

PTGER4 primer set 2
primer 1: SEQ ID NO 59:
5'-TGGGTATTGTAGTCGCGAGTTATC-3' primer 2: SEQ ID NO 60:
5'-CTACGTAAACAAACGATTAACG-3' blocking primer: SEQ ID NO 61:
5'-TGTGAGTTATTGAGATTTATGTTGGGTAGTGT-C3-3' probe: SEQ ID NO 62:
5'-JOE-CAATCTATACGTCCAACGTACTCTTTTACGCGCTA-BHQ1-3'

RARB primer set 1
primer 1: SEQ ID NO 63:
5'-GCGTATAGAGGAATTTAAAGTGTGG-3' primer 2: SEQ ID NO 64:
5'-ACGCCTTTTTATTTACGACGACTTAAC-3' blocking primer: SEQ ID NO 65:
5'-TTATTTACAACAACTTAACTTAAAAAACAATATTCCACC-C3-3' probe: SEQ ID NO 66:
5'-HEX-TATTCCGCCTACGCCCGCTCG-BHQ1-3'

RARB primer set 2
primer 1: SEQ ID NO 67:
5'-GAATTTTTTTATGCGAGTTGTTTGAGG-3' primer 2: SEQ ID NO 68:
5'-TTCCGAATACGTTCCGAATCCTACC-3' blocking primer: SEQ ID NO 69:
5'-TTATGTGAGTTGTTTGAGGATTGGGATGTTGAG-C3-3' probe: SEQ ID NO 70:
5'-HEX-AACAAACCCTACTCGAATCGCTCGCG-BHQ1-3'

RARB primer set 3
primer 1: SEQ ID NO 71:
5'-TGGGAATTTTTCGTTTCGGTT-3' primer 2: SEQ ID NO 72:
5'-ACACGTAAACTATTAATCTTTTTCCCAAC-3' blocking primer: SEQ ID NO 73:
5'-CATAAACTATTAATCTTTTTCCCAACCCCAAATC-C3-3' probe: SEQ ID NO 74:
5'-HEX-TCATTTACCATTTTCCAAACTTACTCGACC-BHQ1-3'

RASSF1A primer set 1
primer 1: SEQ ID NO 75:
5'-GCGTTGAAGTCGGGGTTCG-3' primer 2: SEQ ID NO 76:
5'-CCGATTAAACCCGTACTTC-3'

-continued
blocking primer: SEQ ID NO 77:
5'-TTGGGGTTTGTTTTGTGGTTTCGTTTGGTTTGT-C3-3' probe: SEQ ID NO 78:
5'-JOE-CGCTAACAAACGCGAACCGA-BHQ1-3'

RASSF1A primer set 2
primer 1: SEQ ID NO 79:
5'-GGGAGTTTGAGTTTATTGA-3' primer 2: SEQ ID NO 80:
5'-GATACGCAACGCGTTAACACG-3' blocking primer: SEQ ID NO 81:
5'-CACATTAACACACTCCAACCAAATACAACCCTT-C3-3' probe: SEQ ID NO 82:
5'-JOE-CGCCCAACGAATACCAACTCC-BHQ1-3'

Septin9 primer set 1
primer 1: SEQ ID NO 83:
5'-CGCGATTCGTTGTTTATTAG-3' primer 2: SEQ ID NO 84:
5'-CACCTTCGAAATCCGAAA-3 blocking primer: SEQ ID NO 85:
5'-AAAATCCAAAATAATCCCATCCAACTACACATTAAC-C3-3' probe: SEQ ID NO 86:
5'-FAM-CGCGTTAACCGCGAAATCCGACATAAT-BHQ1-3'

Septin9 primer set 2
primer 1: SEQ ID NO 87:
5'-TAGCGTATTTTCGTTTCGC-3' primer 2: SEQ ID NO 88:
5'-CGAACTTCGAAAATAAATACTAAAC-3 blocking primer: SEQ ID NO 89: 5'-
TTTGTTTTGTGTTAGGTTTATTTGTAGGGTTT-C3-3' probe: SEQ ID NO 90:
5'-FAM-AACTACTACGACCGCGAACGTA-BHQ1-3'

SHOX2 primer set 1
primer 1: SEQ ID NO 91:
5'-GTTCGTGCGATTTCGGTC-3' primer 2: SEQ ID NO 92:
5'-TCGCTACCCCTAAACTCGA -3' blocking primer: SEQ ID NO 93:
5'-TGATTTTGGTTGGGTAGGTGGGATG-C3-3' probe: SEQ ID NO 94:
5'-FAM-CAACCAAATAATCTCCGTCCCGC-BHQ1-3'

SHOX2 primer set 2
primer 1: SEQ ID NO 95:
5'-GGCGGGCGAAAGTAATC-3' primer 2: SEQ ID NO 96:
5'-CGAAAATCGCGAATATTCCG-3' blocking primer: SEQ ID NO 97:
5'-ACAAATATTCCACTTAAACCTATT

AATCTCTATAAATTAAACA-C3-3'
probe: SEQ ID NO 98:
5'-FAM-AAAATCGAATCTACGTTTCCACGAAAA-BHQ1-3' internal reference gene ACTB primers
and probe combination
primer 1: SEQ ID NO 99:
5'-GTGATGGAGGAGGTTTAGTAAGT-3' primer 2: SEQ ID NO 100:
5'-CCAATAAAACCTACTCCTCCCTT-3' probe: SEQ ID NO 101:
5'-CY5-ACCACCACCCAACACACAATAACAAACACA-BHQ3-3'

All of the multiple sets of primers and probes could distinguish between methylated and unmethylated templates, and could be used as primers and probes to detect the methylations of BCAT1, CDH1, DCLK1, FOXL2, HOXA9, PTGER4, RARB, RASSF1A, Septin9 and SHOX2 genes, respectively. Although the effectiveness of different primer and probe combinations were slightly different, the above primers and probes were suitable for the detection of methylations of BCAT1, CDH1, DCLK1, FOXL2, HOXA9, PTGER4, RARB, RASSF1A, Septin9 or SHOX2 genes, respectively. Table 1 below showed the detection results of methylated and unmethylated templates (treated with bisulfite) of the above genes with various primer and probe combinations. Obviously, the designed primer and probe combinations were highly specific for the methylated templates.

TABLE 1 detection results of the designed primer sets on methylated and unmethylated templates (Ct, mean)

| | BCAT1-1 | BCAT1-2 | CDH1-1 | CDH1-2 | DCLK1-1 | DCLK1-2 | FOXL2-1 | FOXL2-2 | FOXL2-3 | HOXA9-1 | HOXA9-2 |
|---|---|---|---|---|---|---|---|---|---|---|---|
| methylated DNA | 34.12 | 31.24 | 29.88 | 32.20 | 33.72 | 30.34 | 29.39 | 31.98 | 28.72 | 27.83 | 29.81 |
| unmethylated DNA | No Ct | No Ct | No Ct | No Ct | No Ct | No Ct | No Ct | No Ct | No Ct | No Ct | No Ct |

| | PTGER4-1 | PTGER4-2 | RARB-1 | RARB-2 | RARB-3 | RASSF1A-1 | RASSF1A-2 | Septin9-1 | Septin9-2 | SHOX2-1 | SHOX2-2 |
|---|---|---|---|---|---|---|---|---|---|---|---|
| methylated DNA | 31.34 | 30.01 | 29.36 | 31.34 | 30.22 | 28.67 | 27.78 | 30.26 | 27.89 | 27.37 | 29.53 |
| unmethylated DNA | No Ct | No Ct | No Ct | No Ct | No Ct | No Ct | No Ct | No Ct | No Ct | No Ct | No Ct |

Furthermore, DNAs from different cancer patients and healthy people were used as templates to further verify the effectiveness of the primer and probe combinations. DNAs in plasma samples from 5 cases of lung cancer, 3 cases of liver cancer, and 5 cases of healthy persons were extracted by using the DNA extraction method of Example 1, and then DNA templates were treated with bisulfite by using the method of Example 2. Using the above-mentioned multiple primer and probe sets, real-time fluorescent PCR experiments were performed. The Ct values of various marker genes in cancer samples and healthy person samples were measured respectively. The results were shown in Table 2.

healthy person samples. Therefore, all of the above primer sets were suitable for lung cancer detection.

Example 4: Sensitivity and Specificity of the Kit for Detecting the Plasmas of Lung Cancer Patients and Benign Patients 168 samples from patients with pathologically identified lung cancer and 264 samples from patients with pathologically identified benign disease were used (see Table 3). All of the samples were collected from the Naval General Hospital of People's Liberation Army. The lung cancer

TABLE 2 detection results of the methylation levels of the specified genes in individuals with known lung cancer status (including healthy individuals) with each primer set

| | BCAT1-1 | BCAT1-2 | CDH1-1 | CDH1-2 | DCLK1-1 | DCLK1-2 | FOXL2-1 | FOXL2-2 | FOXL2-3 | HOXA9-1 | HOXA9-2 |
|---|---|---|---|---|---|---|---|---|---|---|---|
| LuCa 1 | 35.88 | 33.93 | 36.34 | 33.27 | 36.77 | 34.51 | 33.37 | 34.13 | 31.57 | 37.25 | 33.23 |
| LuCa 2 | 39.28 | 34.92 | 35.77 | 35.32 | 34.91 | 35.09 | 36.68 | 35.02 | 34.21 | 36.67 | 33.67 |
| LuCa 3 | 35.31 | 29.62 | 36.12 | 34.56 | 35.42 | 31.74 | 34.21 | 32.58 | 29.92 | 32.51 | 26.43 |
| LuCa 4 | 35.45 | 36.59 | 33.89 | 30.41 | 34.35 | 34.81 | 31.53 | 39.29 | 34.73 | 31.49 | 31.37 |
| LuCa 5 | 34.84 | 36.91 | 36.92 | 38.99 | 32.56 | 35.09 | 33.62 | 35.87 | 39.15 | 34.09 | 35.33 |
| HeCa 1 | No Ct | 43.53 | No Ct | 40.16 | 41.56 | 43.65 | No Ct | No Ct | 42.15 | No Ct | 41.67 |
| HeCa 2 | No Ct | No Ct | 42.32 | No Ct | No Ct | No Ct | 41.51 | 42.39 | No Ct | 44.57 | No Ct |
| HeCa 3 | 44.46 | No Ct | No Ct | 41.89 | 41.67 | 42.35 | No Ct | No Ct | 44.42 | No Ct | 44.14 |
| Con 1 | No Ct | 44.21 | No Ct | 42.14 | 42.46 | 44.23 | No Ct | No Ct | No Ct | No Ct | No Ct |
| Con 2 | No Ct | No Ct | 43.12 | No Ct | No Ct | No Ct | 44.34 | 43.32 | No Ct | No Ct | 43.23 |
| Con 3 | No Ct | No Ct | No Ct | No Ct | No Ct | 43.72 | No Ct | No Ct | No Ct | No Ct | No Ct |
| Con 4 | No Ct | No Ct | No Ct | 42.01 | 43.35 | No Ct | No Ct | 43.12 | No Ct | 44.56 | No Ct |
| Con 5 | No Ct | No Ct | 42.38 | No Ct | No Ct | No Ct | 43.36 | No Ct | No Ct | No Ct | No Ct |

| | PTGER4-1 | PTGER4-2 | RARB-1 | RARB-2 | RARB-3 | RASSF1A-1 | RASSF1A-2 | Septin9-1 | Septin9-2 | SHOX2-1 | SHOX2-2 |
|---|---|---|---|---|---|---|---|---|---|---|---|
| LuCa 1 | 35.88 | 31.63 | 33.73 | 31.89 | 37.03 | 36.11 | 29.06 | 31.28 | 31.57 | 37.25 | 31.21 |
| LuCa 2 | 35.57 | 32.36 | 32.16 | 30.56 | 35.16 | 30.19 | 30.82 | 31.78 | 34.21 | 36.67 | 31.27 |
| LuCa 3 | 33.43 | 27.62 | 33.51 | 29.56 | 32.32 | 38.46 | 34.11 | 35.35 | 31.23 | 32.51 | 32.32 |
| LuCa 4 | 35.11 | 32.34 | 32.87 | 30.41 | 29.64 | 31.16 | 34.13 | 32.42 | 31.89 | 31.49 | 31.24 |
| LuCa 5 | 30.34 | 32.73 | 32.23 | 28.36 | 31.65 | 31.29 | 28.32 | 31.76 | 29.11 | 34.09 | 29.78 |
| HeCa 1 | No Ct | 42.99 | 41.56 | 41.16 | 40.96 | 42.16 | No Ct | No Ct | 42.51 | No Ct | No Ct |
| HeCa 2 | No Ct | No Ct | 44.45 | 43.88 | No Ct | 43.45 | 40.98 | 43.21 | 42.12 | 42.53 | 42.51 |
| HeCa 3 | 44.46 | 43.67 | No Ct | 41.29 | 42.36 | 42.35 | No Ct | 44.12 | 42.42 | 44.33 | 43.21 |
| Con 1 | No Ct | 44.01 | No Ct | No Ct | 43.43 | 44.13 | No Ct | No Ct | No Ct | No Ct | 44.15 |
| Con 2 | No Ct | No Ct | No Ct | No Ct | No Ct | No Ct | 43.14 | 44.21 | No Ct | No Ct | No Ct |
| Con 3 | 42.12 | No Ct | No Ct | No Ct | No Ct | No Ct | No Ct | No Ct | No Ct | 44.23 | No Ct |
| Con 4 | No Ct | 43.19 | 43.23 | No Ct | No Ct | No Ct | No Ct | 43.35 | No Ct | No Ct | 43.76 |
| Con 5 | No Ct | No Ct | No Ct | No Ct | No Ct | No Ct | No Ct | No Ct | No Ct | No Ct | No Ct | abbreviations: LuCa: lung cancer; HeCa: liver cancer; Con: healthy

As can be seen from the above detected Ct values of the methylations of BCAT1, CDH1, DCLK1, FOXL2, HOXA9, PTGER4, RARB, RASSF1A, Septin9, and SHOX2 genes, each primer and probe combination above generated a highly specific amplification for methylated DNA of lung cancers, while there were no amplification or the Ct values of the amplifications are greater than 40 for other cancers or the healthy persons. Although the Ct values of the amplifications for lung cancer samples with different combinations of primer pair and probe showed some differences, they were obviously different from those of other cancers and samples included all stages and common subtypes of the disease. The lung cancer patients were confirmed by imaging and pathological diagnosis. The sample staging was based on international TNM staging standards, and the sample subtyping was determined according to tissue biopsies and immunohistochemical methods. Benign samples included common types of benign disorders founded in the whole study population. Complete clinical pathology reports were obtained after surgeries, including patient's age, smoking history, race, stage, subtype, and the collection sites were encoded for each sample.

TABLE 3 lung cancer stages and other characteristics of the collected samples

|  | lung cancer = stage and subtype | | | | | benign |
|---|---|---|---|---|---|---|
|  | I | II | III | IV | total |  |
| number of samples (%) |  |  |  |  |  | — |
| lung cancer |  |  |  |  |  | — |
| adenocarcinoma | 7 | 19 | 45 | 14 | 85(50.9) | — |
| squamous cell | 4 | 6 | 19 | 9 | 38(22.8) | — |
| large cell lung | 3 | 4 | 5 | 3 | 15(9.0) | — |
| small cell lung cancer | 3 | 5 | 19 | 2 | 29(17.4) | — |
| sum | 17 (10.2) | 34 (20.4) | 88 (52.7) | 29 (16.8) | 168 (100) | — |
| benign |  |  |  |  |  |  |
| nodule | — | — | — | — | — | 85(32.2) |
| cyst | — | — | — | — | — | 91(34.5) |
| mixed | — | — | — | — | — | 65(24.6) |
| no abnormalities | — | — | — | — | — | 23(8.7) |
| sum | — | — | — | — | — | 264(100) |
| ages of the population |  |  |  |  |  |  |
| median age(years) | 58 | 60 | 62 | 68 | 60 | 50 |
| age range(years) | 33-80 | 43-85 | 39-83 | 35-85 | 33-85 | 18-80 |
| mean age(years) | 59.8 | 62.9 | 61.5 | 65.7 | 61.3 | 51.5 |
| SD | 12.4 | 11.3 | 9.8 | 10.5 | 9.9 | 12.5 |
| median smoking index(SI) | 220 | 190 | 230 | 270 | 200 | 90 |
| smoking index range(SI) | 0-460 | 0-480 | 0-550 | 0-610 | 0-610 | 0-430 |
| mean smoking index(SI) | 203 | 224 | 325 | 297 | 318 | 103 |
| SD | 15.6 | 14.1 | 13.1 | 15.2 | 13.9 | 12.3 |

DNAs were extracted from the samples by using the DNA extraction method of Example 1, the DNA templates were then treated with bisulfite by using the method of Example 2, and, next, real-time fluorescent PCR experiments were performed with the primer and probe combinations provided in Example 3 (for each biomarker gene, primer set 1 was used) to detect BCAT1, CDH1, DCLK1, FOXL2, HOXA9, PTGER4, RARB, RASSF1A, Septin9 and SHOX2 genes and internal reference gene ACTB and the Ct values were obtained for each gene from healthy persons and lung cancer patients. As described in Example 3 above, the methylation level of each gene could be indicated by these Ct values.

Commercially available software packages (IBM SPSS Statistics 24 and MedCalc 11.4.2.0, purchased from IBM and MedCalc) were used for descriptive statistics of plasma biomarker levels, receiver operating characteristic (ROC) curves and graphical displays. The nonparametric Kruskal-Wallis test (ANOVA) was used, and then a Dunn's multiple comparison post-test was used to determine statistical differences. For all statistical comparisons, a P value <0.05 is considered statistically significant.

The methylation levels of the above 10 marker genes were detected in plasmas from 168 patients with pathologically determined lung cancer and 264 individuals with benign lung disorders by real-time fluorescent PCR assays. To facilitate the determination of the ability of these biomarker genes to distinguish cancers from benign lung disorders with similar symptoms, all samples were obtained from the same clinical population (based on patients who have undergone surgeries for pulmonary nodules). All samples were collected before any intervention and before the disease status was known. The disease status was then determined by pathological examination of the isolated tissues. A single sample collection protocol was used to collect the plasmas and compliance was monitored. This ensured sample quality and eliminated any possibility of collection, processing and biological bias in the sample set. Normal healthy samples were not used in this study because they are usually more easily distinguishable than benign disorders. These samples showed that the average patient age among individuals with lung cancers (61 years) was higher than that among individuals with benign disorders (51 years), the average smoking index among individuals with lung cancers (318) was higher than that among individuals with benign disorders (103), and both increased with the progression of disease staging. Overall, the distribution of lung cancer subtypes was similar to that found in all lung cancer cases in the population, with the proportion (83%) of non-small cell lung cancers (including adenocarcinomas, squamous cell carcinomas, and large cell carcinomas) being larger than that of small cell lung cancers (Table 3). The benign controls in the study represented common benign lung diseases, including benign nodules and cysts.

For the detected data of the methylation levels of each biomarker, MedCalc 11.4.2.0 software was used to generate a ROC curve and an area under the curve (AUC) value with selection of a 95% confidence interval. Compared with benign lung disorders, the AUCs of the methylation levels of 10 biomarker genes in lung cancer samples were all greater than 0.8 (P value >0.05), and ranged from 0.80 to 0.92 (see FIG. 1 and Table 4).

TABLE 4 areas under the curves (AUCs) though curve analysis of the receiver operating characteristic (ROC) curves of 10 marker genes.

| markers | AUC | standard error | 95% CI |
|---|---|---|---|
| BCAT1 | 0.919 | 0.013 | 0.895 to 0.948 |
| CDH1 | 0.825 | 0.023 | 0.781 to 0.863 |
| DCLK1 | 0.885 | 0.022 | 0.840 to 0.921 |
| FOXL2 | 0.838 | 0.021 | 0.795 to 0.881 |

TABLE 4-continued areas under the curves (AUCs) though curve analysis of the receiver operating characteristic (ROC) curves of 10 marker genes.

| markers | AUC | standard error | 95% CI |
|---|---|---|---|
| HOXA9 | 0.859 | 0.019 | 0.822 to 0.889 |
| PTGER4 | 0.845 | 0.025 | 0.801 to 0.892 |
| RARB | 0.831 | 0.016 | 0.793 to 0.877 |
| RASSF1A | 0.879 | 0.023 | 0.832 to 0.911 |
| Septin9 | 0.809 | 0.024 | 0.762 to 0.849 |
| SHOX2 | 0.886 | 0.023 | 0.841 to 0.922 |

Figure 2A:
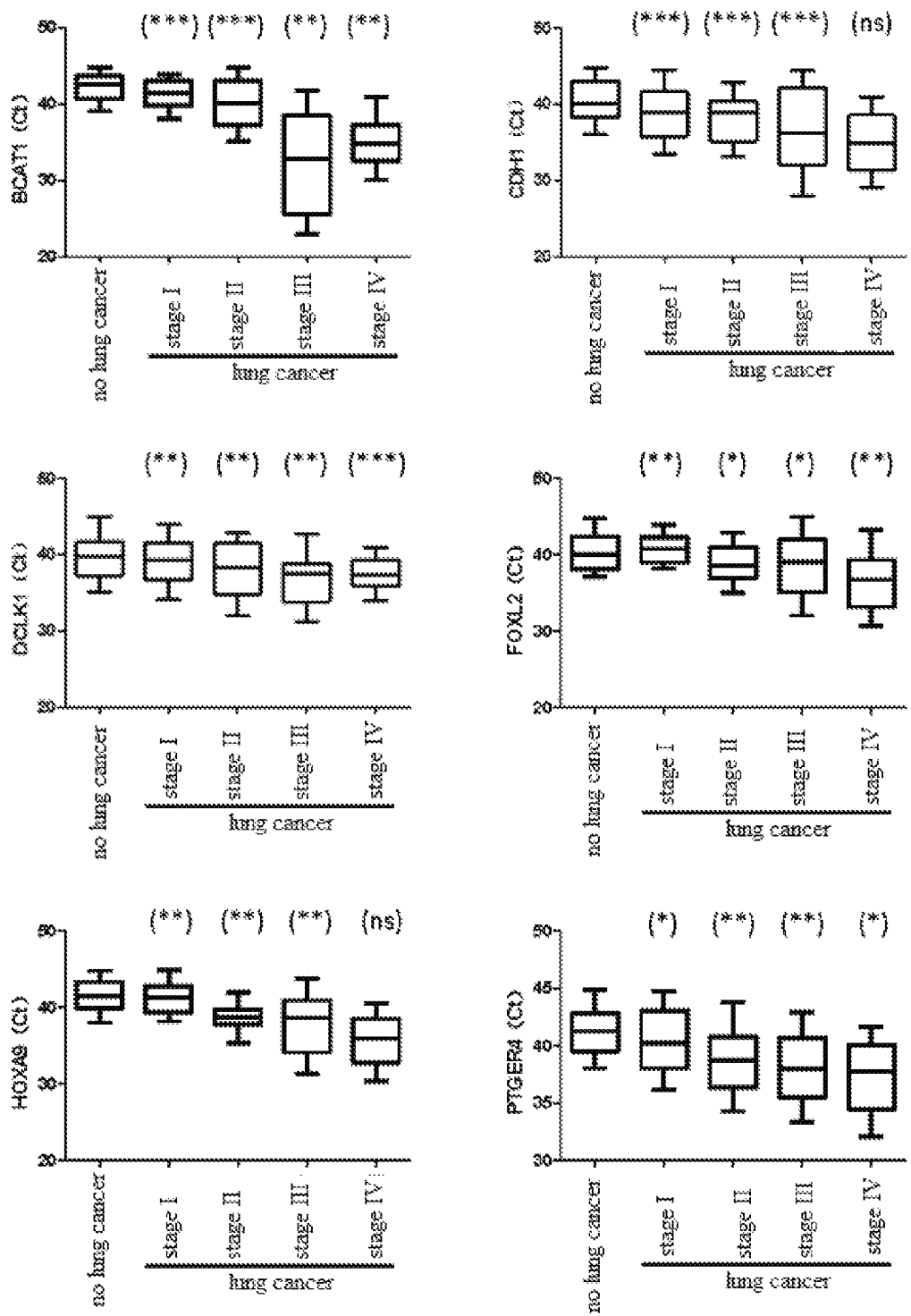
FIGS. 2A and 2B show the methylation level distribution of 10 biomarker genes in different lung cancer stages.
Figure 2B:
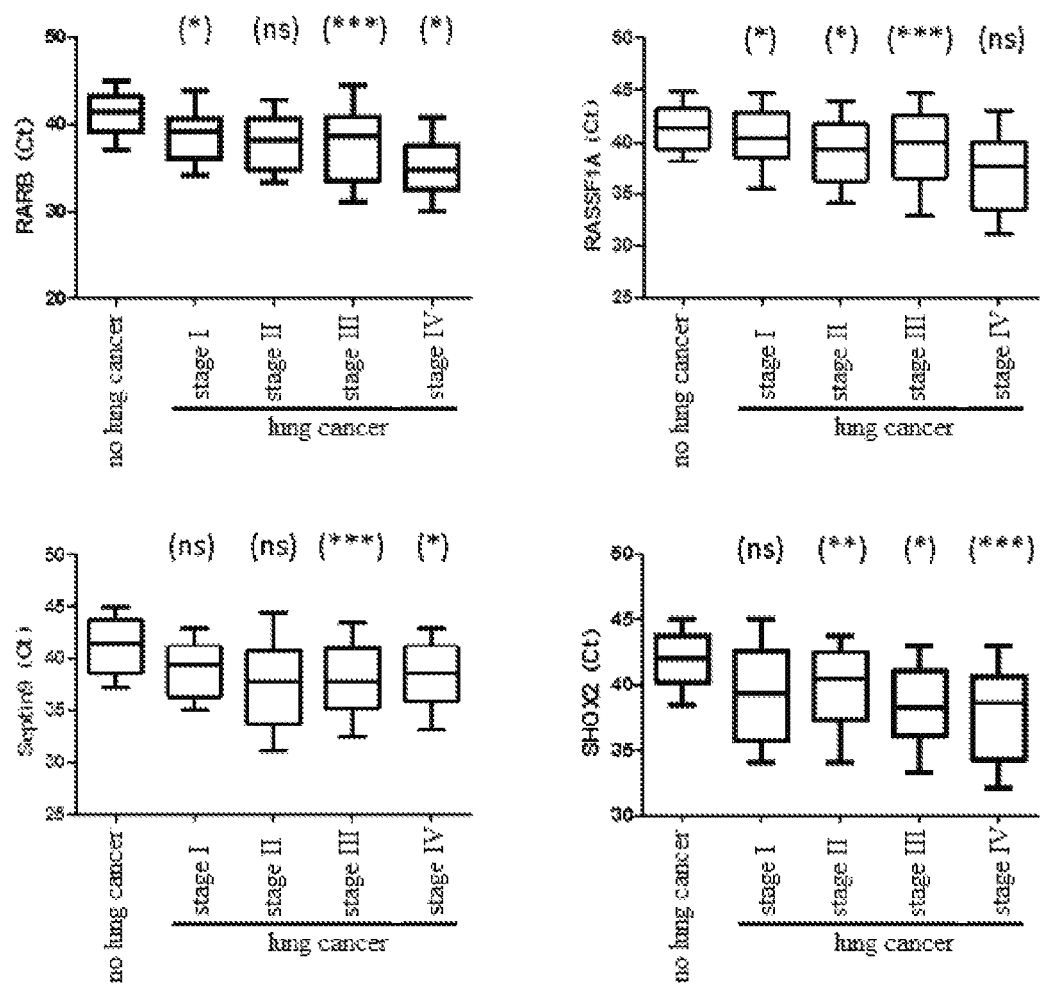

In order to determine whether certain biomarker genes could provide a better distinguishing ability between different stages of lung cancers (especially in early stages), the distinguishing abilities of the methylation levels of 10 biomarker genes (FIGS. 2A and 2B) in stage I and stage II samples (the most important period for the marker detections) were compared. For stage I samples, both BCAT1 and CDH1 provided very high distinguishing abilities (P value <0.001), followed by FOXL2, HOXA9 and DCLK1 (P value 0.001 to 0.01) in descending order, and then RASSF1A, PTGER4 and RARB (P Value 0.01 to 0.05). For Septin9 and SHOX2, there were no significant differences between stage I cancers and benign diseases (P value>0.05). For stage II samples, both BCAT1 and CDH1 again provided very high distinguishing abilities (P value <0.001), followed by DCLK1, HOXA9, PTGER4 and SHOX2 (P value 0.001 to 0.01), and then FOXL2 and RASSF1A (P value 0.01 to 0.05). There were no significant differences for RARB and Septin9 (P value>0.05).

Figure 3A:
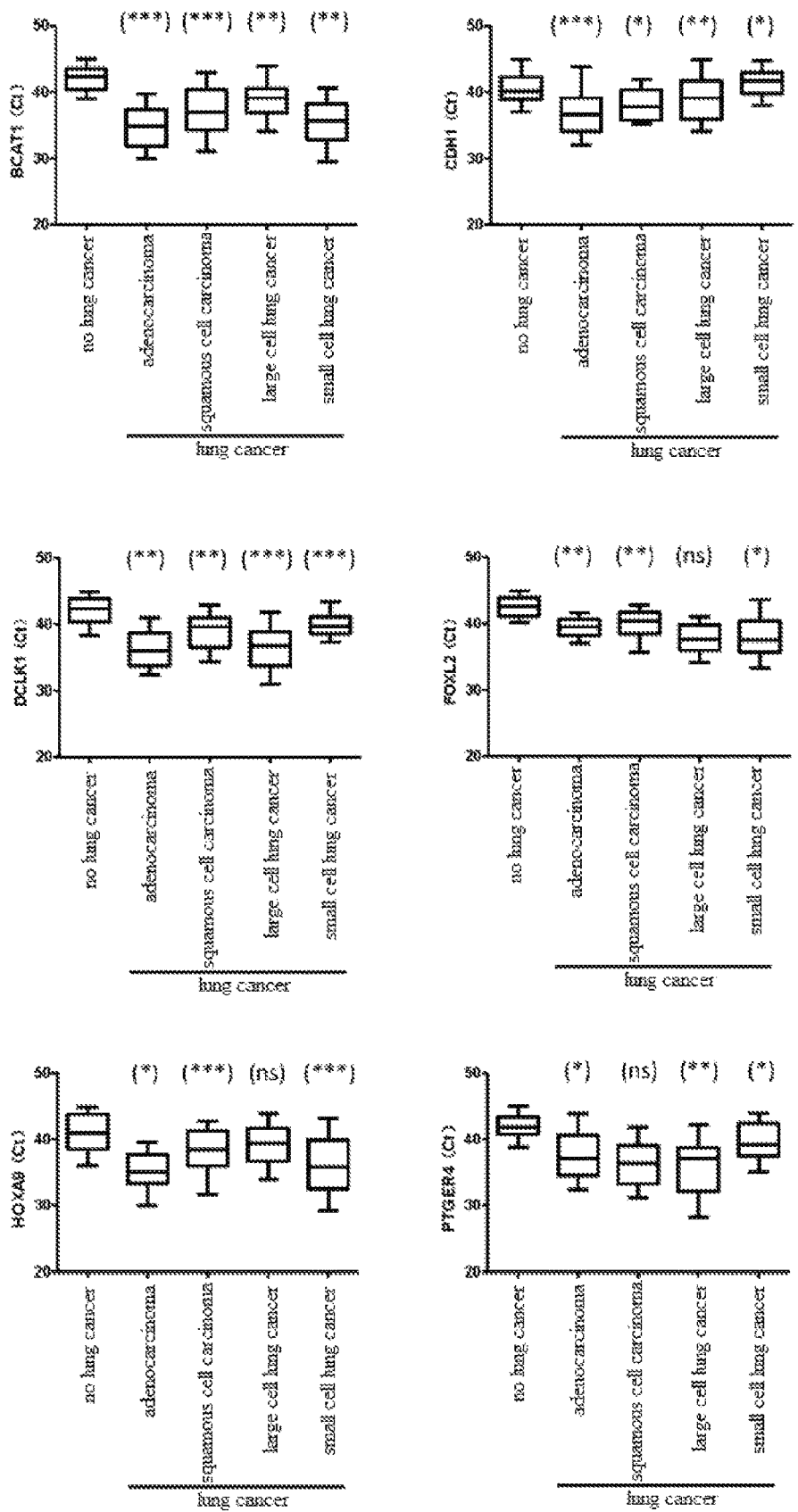
FIGS. 3A and 3B show the methylation level distribution of 10 biomarker genes in different lung cancer subtypes.
Figure 3B:
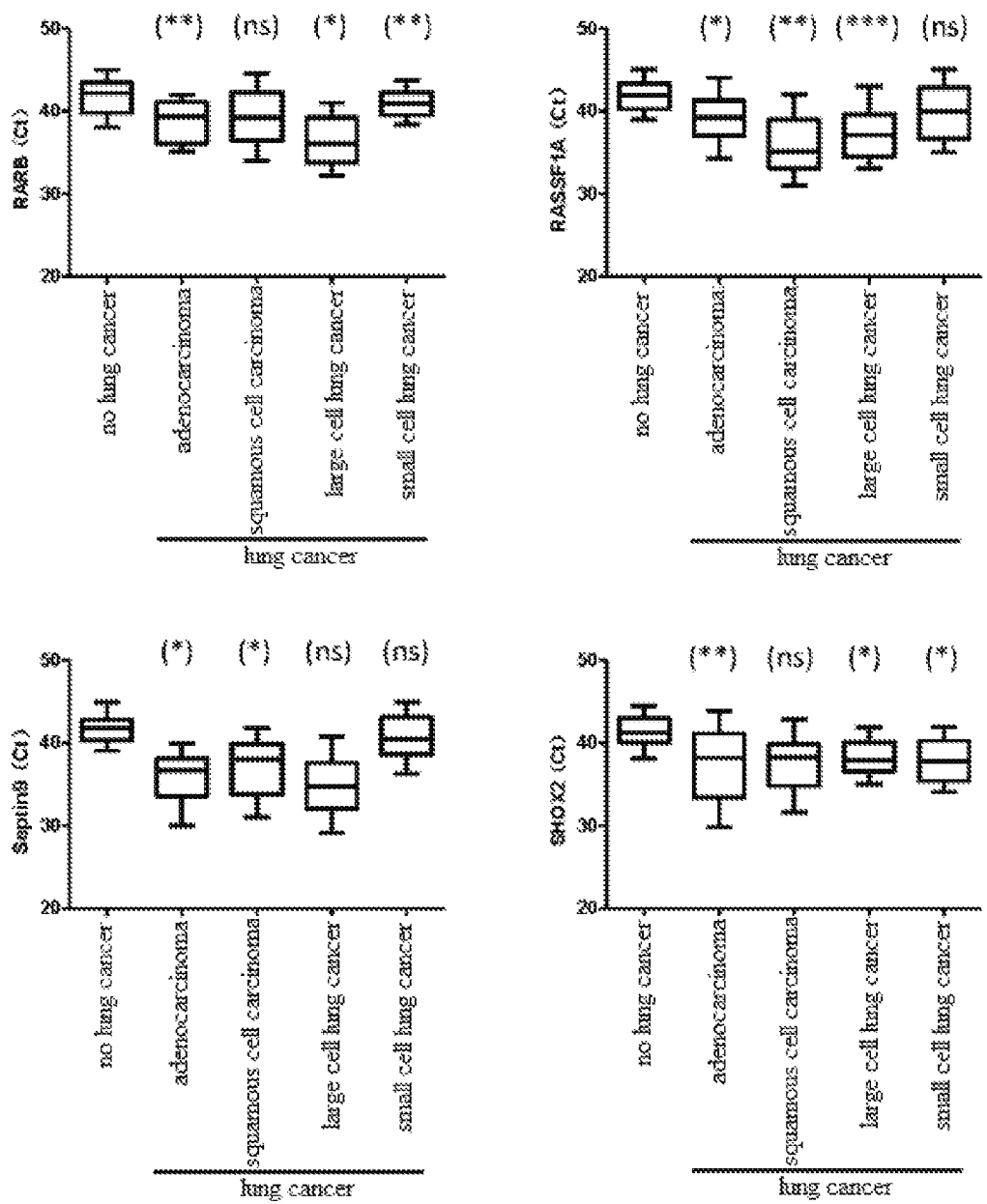

It was also evaluated whether there were statistically significant differences in the methylation levels of the above biomarker genes between samples from benign disorders and various subtypes of lung cancers (FIGS. 3A and 3B). For adenocarcinomas, both BCAT1 and CDH1 provided very high distinguishing abilities (P value <0.001), followed by FOXL2, DCLK1, RARB, SHOX2, RASSF1A, PTGER4, HOXA9 and Septin9 (P Value 0.001 to 0.05) in descending order. For squamous cell carcinomas, BCAT1 and HOXA9 provided very high distinguishing abilities (P value <0.001), followed by DCLK1, FOXL2, RASSF1A and Septin9 (P Value 0.001 to 0.05). For large cell carcinomas, DCLK1 and RASSF1A provided very high distinguishing abilities (P value <0.001), followed by BCAT1, CDH1, PTGER4, SHOX2 and RARB (P Value 0.001 to 0.05) in descending order. For small cell lung cancers, DCLK1 and HOXA9 provide very high distinguishing abilities (P value <0.001), followed by BCAT1, RARB, CDH1, PTGER4, SHOX2 and FOXL2 (P Value 0.001 to 0.05) in descending order.

In terms of simple operation and cost reduction, the detection of the methylation level of a single biomarker gene is better than the detection the methylation levels of multiple biomarker genes. However, it is obvious that the methylation level of a single biomarker gene may not provide information on the inherent diversity of a complex disease, so it is often necessary to establish a diagnostic model with multiple markers. Multi-marker diagnosis model is established by using statistical analysis methods. The establishment of a diagnosis model with methylated gene markers for the detection of lung cancers is described below by taking a logistic regression model as an example.

The training of the logistic regression model was conducted as follows: dividing the samples into cases and controls, and then optimizing the regression coefficients with IBM SPSS Statistics 24 software. Maximum likelihood of the data was trained with the logistic regression model by using one regression coefficient for each marker and one deviation parameter.

After training, the regression coefficient set defined the logistic regression model. By putting the methylation levels of the biomarkers into the logistic regression equation, those skilled in the art can easily use such diagnostic model to predict the possibility of any new sample to be identified as a case or a control.

Figure 4:
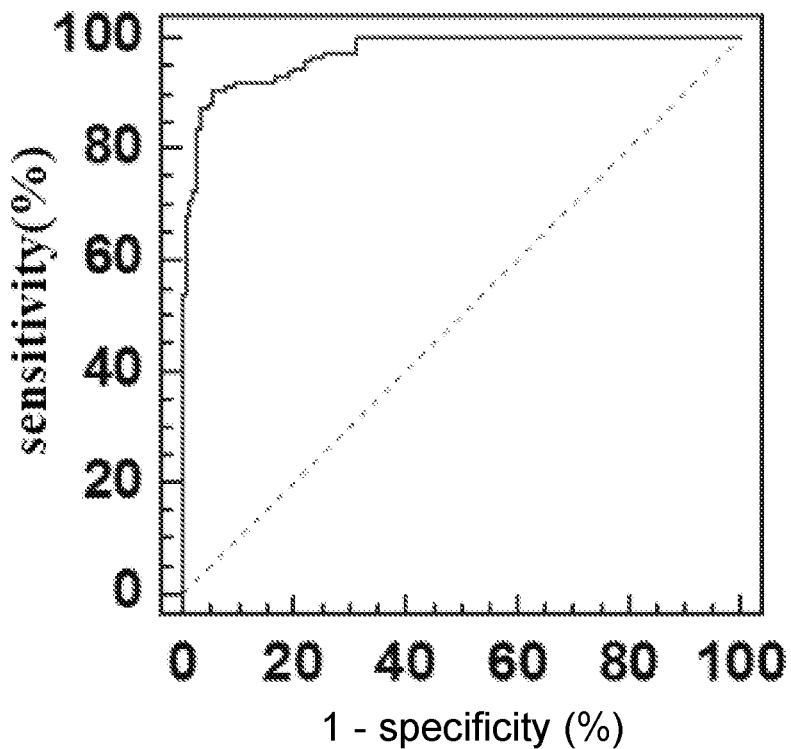
FIG. 4 shows the receiver operating characteristic (ROC) curve of a logistic regression model constructed with 10 marker genes.
Figure 5:
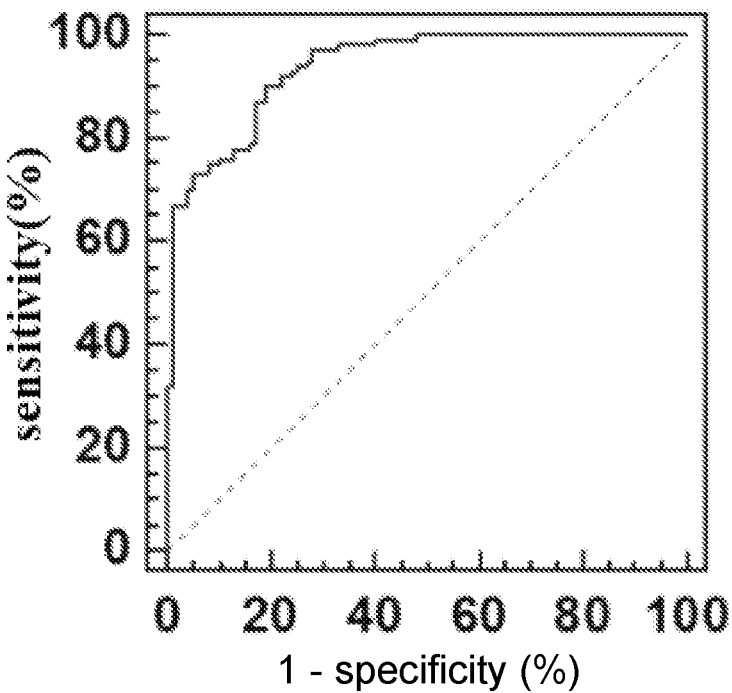
FIG. 5 shows the receiver operating characteristic (ROC) curve of a logistic regression model constructed with the five most characteristic marker genes.

The AUCs obtained of the above 10 marker genes were all greater than 0.80. Next, the logistic regression was used to combine the 10 marker genes, which generated an AUC of 0.950 (standard error: 0.01213; 95% CI: 0.926-0.974; P value: <0.0001) (FIG. 4). In order to simplify the monitoring and analysis method, the five markers with larger AUC valueswere combined and used to establish a logistic regression model. The obtained AUC value was 0.938 (standard error: 0.0152; 95% CI: 0.895-0.967; P value: <0.0001) (FIG. 5). For this sample set, a 98.0% sensitivity was acquired at a specificity of 43.9%. Two models were further compared by determining a model's sensitivity at a fixed specificity value and a model's specificity at a fixed sensitivity value (see Tables 5 and 6 below). For example, It could be selected that, when the sensitivity of the method was greater than about 95%, the sum of its sensitivity and specificity was greater than about 150%; or when the specificity of the method was greater than about 95%, the sum of its sensitivity and specificity was greater than about 170%. Generally, the sensitivity and specificity of a logistic regression model with 10 markers were slightly better than that with 5 markers. However, when the operational analysis procedures and cost were taken into consideration, the combination of the 5 markers might also be a good choice.

TABLE 5 sensitivities at important specificity thresholds in logistic regression models of the 5 most characteristic marker genes and of 10 marker genes

| specificity thresholds | sensitivity (%) | |
|---|---|---|
| | 5 markers | 10 markers |
| 80 | 90.2 | 85.8 |
| 85 | 78.7 | 83.2 |
| 90 | 75.1 | 79.8 |
| 95 | 58.6 | 77.9 |
| 100 | 32.8 | 61.2 |

TABLE 6 specificities at important sensitivity thresholds in logistic regression models of the 5 most characteristic marker genes and of 10 marker genes

| sensitivity thresholds | specificity (%) | |
|---|---|---|
| | 5 markers | 10 markers |
| 80 | 83.3 | 88.3 |
| 85 | 81.3 | 83.9 |
| 90 | 78.1 | 79.5 |
| 95 | 76.6 | 78.3 |
| 100 | 52.9 | 59.5 |

It should be noted that the detection results of the methylation levels provided in this Example were obtained with primer set 1 for each biomarker gene (for example, for BCAT1 gene, use BCAT1 primer set 1; for CDH1 gene, use CDH1 primer set 1, and so on), and similar detection results were obtained with other primer sets provided herein (data not shown).

The technical solutions provided by the present disclosure, through jointly detecting the methylation levels of one or more genes of BCAT1, CDH1, DCLK1, FOXL2, HOXA9, PTGER4, RARB, RASSF1A, Septin9 and SHOX2 genes or fragments thereof, improved the sensitivity and specificity of lung cancer detection, and thus it ensured the accuracy and reliability of the test results. Moreover, the method for the detection of methylated DNAs of biomarker genes in a sample was able to easily accomplish the detection of the methylation levels of 10 biomarkers: BCAT1, CDH1, DCLK1, FOXL2, HOXA9, PTGER4, RARB, RASSF1A, Septin9 and SHOX2 genes, quickly and conveniently determine whether the sample was positive or not and the risk value by using a logistic regression equation, and provide a kit for rapid detection of the cancer.

The above Examples are only used to illustrate the technical solutions of the present disclosure and not to limit them. It will be understood by those of ordinary skill in the art that the technical solutions described in the foregoing Examples can be modified, or some or all of the technical features can be replaced equivalently. These modifications or replacements do not deviate the essence of the corresponding technical solutions from the scope of the technical solutions of the Examples of the present disclosure, and they should all be encompassed within the scope of the present specification.

What is claimed is:

1. A method for identifying a lung cancer status in a subject comprising:
   1) detecting methylation levels of biomarker genes in biological samples from multiple patients with known lung cancer status and constructing a logistic regression diagnostic model with the methylation levels; and
   2) detecting methylation levels of the biomarker genes in a biological sample of the subject, and determining the lung cancer status in the subject with the logistic regression diagnostic model, wherein the biomarker genes comprise: BCAT1, DCLK1, HOXA9, RASSF1A, and SHOX2 and the biological sample is plasm; and
   wherein the detection of the methylation level of the BCAT1 gene comprises the use of a primer pair having the sequences as set forth in SEQ ID NOs: 11 and 12 and a blocking primer having the sequence as set forth in SEQ ID NO: 13 to carry out a PCR amplification reaction, with the bisulfate-treated BCAT1 gene or a fragment thereof in the biological sample as a template; the detection of the methylation level of the DCLK1 gene comprises the use of a primer pair having the sequences as set forth in SEQ ID NOs: 27 and 28 and a blocking primer having the sequence as set forth in SEQ ID NO: 29 to carry out a PCR amplification reaction, with the bisulfate-treated DCLK1 gene or a fragment thereof in the biological sample as a template; the detection of the methylation level of the HOXA9 gene comprises the use of a primer pair having the sequences as set forth in SEQ ID NOs: 47 and 48 and a blocking primer having the sequence as set forth in SEQ ID NO: 49 to carry out a PCR amplification reaction, with the bisulfite-treated HOXA9 gene or a fragment thereof in the biological sample as a template; the detection of the methylation level of the RASSF1A gene comprises the use of a primer pair having the sequences as set forth in SEQ ID NOs: 75 and 76 and a blocking primer having the sequence as set forth in SEQ ID NO: 77 to carry out a PCR amplification reaction, with the bisulfate-treated RASSF1A gene or a fragment thereof in the biological sample as a template; the detection of the methylation level of the Septin9 gene comprises the use of a primer pair having the sequences as set forth in SEQ ID NOs: 83 and 84 and a blocking primer having the sequence as set forth in SEQ ID NO: 85 to carry out a PCR amplification reaction, with the bisulfate-treated Septin9 gene or a fragment thereof in the biological sample as a template; and the detection of the methylation level of the SHOX2 gene comprises the use of a primer pair having the sequences as set forth in SEQ ID NOs: 91 and 92 and a blocking primer having the sequence as set forth in SEQ ID NO: 93 to carry out a PCR amplification reaction, with the bisulfate-treated SHOX2 gene or a fragment thereof in the biological sample as a template, wherein the biological sample is plasma, and wherein the step 3) comprises determining the colorectal cancer state in the subject according to the methylation levels of the biomarker genes based on a logistic regression.

2. The method of claim 1, wherein the lung cancer status includes a presence of the lung cancer.

3. The method of claim 1, wherein the bisulfite is sodium bisulfite.

4. The method of claim 1, wherein the biomarker genes are: BCAT1, CDH1, DCLK1, FOXL2, HOXA9, PTGER4, RARB, RASSF1A, Septin9, and SHOX2, and the detection of the methylation level of the BCAT1 gene comprises the use of a primer pair having the sequences as set forth in SEQ ID NOs: 11 and 12 and a blocking primer having the sequence as set forth in SEQ ID NO: 13 to carry out a PCR amplification reaction, with the bisulfate-treated BCAT1 gene or a fragment thereof in the biological sample as a template; the detection of the methylation level of the CDH1 gene comprises the use of a primer pair having the sequences as set forth in SEQ ID NOs: 19 and 20 and a blocking primer having the sequence as set forth in SEQ ID NO: 21 to carry out a PCR amplification reaction, with the bisulfite-treated CDH1 gene or a fragment thereof in the biological sample as a template; the detection of the methylation level of the DCLK1 gene comprises the use of a primer pair having the sequences as set forth in SEQ ID NOs: 27 and 28 and a blocking primer having the sequence as set forth in SEQ ID NO: 29 to carry out a PCR amplification reaction, with the bisulfate-treated DCLK1 gene or a fragment thereof in the biological sample as a template; the detection of the methylation level of the FOXL2 gene comprises the use of a primer pair having the sequences as set forth in SEQ ID NOs: 35 and 36 and a blocking primer having the sequence as set forth in SEQ ID NO: 37 to carry out a PCR amplification reaction, with the bisulfate-treated FOXL2 gene or a fragment thereof in the biological sample as a template; the detection of the methylation level of the HOXA9 gene comprises the use of a primer pair having the sequences as set forth in SEQ ID NOs: 47 and 48 and a blocking primer having the sequence as set forth in SEQ ID NO: 49 to carry out a PCR amplification reaction, with the bisulfate-treated HOXA9 gene or a fragment thereof in the biological sample as a template; the detection of the methylation level of the PTGER4 gene comprises the use of a primer pair having the sequences as set forth in SEQ ID NOs: 55 and 56 and a blocking primer having the sequence as set forth in SEQ ID NO: 57 to carry out a PCR amplification reaction, with the bisulfate-treated PTGER4 gene or a fragment thereof in the biological sample as a template; the detection of the methylation level of the RARB gene comprises the use of a primer pair having the sequences as set forth in SEQ ID NOs: 63 and 64 and a blocking primer having the sequence as set forth in SEQ ID NO: 65 to carry out a PCR amplification reaction, with the bisulfate-treated RARB gene or a fragment thereof in the biological sample as a template; the detection of the methylation level of the RASSF1A gene comprises the use of a primer pair having the sequences as set forth in SEQ ID NOs: 75 and 76 and a blocking primer having the sequence as set forth in SEQ ID NO: 77 to carry out a PCR amplification reaction, with the bisulfate-treated RASSF1A gene or a fragment thereof in the biological sample as a template; the detection of the methylation level of the Septin9 gene comprises the use of a primer pair having the sequences as set forth in SEQ ID NOs: 83 and 84 and a blocking primer having the sequence as set forth in SEQ ID NO: 85 to carry out a PCR amplification reaction, with the bisulfate-treated Septin9 gene or a fragment thereof in the biological sample as a template; and the detection of the methylation level of the SHOX2 gene comprises the use of a primer pair having the sequences as set forth in SEQ ID NOs: 91 and 92 and a blocking primer having the sequence as set forth in SEQ ID NO: 93 to carry out a PCR amplification reaction, with the bisulfate-treated SHOX2 gene or a fragment thereof in the biological sample as a template, wherein the blocking primers have a 3' end modification, which prevents extension and amplification of a DNA polymerase.

5. The method of claim 4,
the detection of the methylation level of the BCAT1 gene comprises the use of a primer pair having the sequences as set forth in SEQ ID Nos: 11 and 12, a blocking primer having the sequence as set forth in SEQ ID NO: 13 and a probe having the sequence as set forth in SEQ ID NO: 14 to carry out a PCR amplification reaction, with the bisulfate-treated BCAT1 gene or a fragment thereof in the biological sample as a template;
the detection of the methylation level of the CDH1 gene comprises the use of a primer pair having the sequences as set forth in SEQ ID NOs: 19 and 20, a blocking primer having the sequence as set forth in SEQ ID NO: 21 and a probe having the sequence as set forth in SEQ ID NO: 22 to carry out a PCR amplification reaction, with the bisulfate-treated CDH1 gene or a fragment thereof in the biological sample as a template;
the detection of the methylation level of the DCLK1 gene comprises the use of a primer pair having the sequences as set forth in SEQ ID Nos: 27 and 28, a blocking primer having the sequence as set forth in SEQ ID NO: 29 and a probe having the sequence as set forth in SEQ ID NO: 30 to carry out a PCR amplification reaction, with the bisulfate-treated DCLK1 gene or a fragment thereof in the biological sample as a template;
the detection of the methylation level of the FOXL2 gene comprises the use of a primer pair having the sequences as set forth in SEQ ID NOs: 35 and 36, a blocking primer having the sequence as set forth in SEQ ID NO: 37 and a probe having the sequence as set forth in SEQ ID NO: 38 to carry out a PCR amplification reaction, with the bisulfate-treated FOXL2 gene or a fragment thereof in the biological sample as a template;
the detection of the methylation level of the HOXA9 gene comprises the use of a primer pair having the sequences as set forth in SEQ ID NOs: 47 and 48, a blocking primer having the sequence as set forth in SEQ ID NO: 49 and a probe having the sequence as set forth in SEQ ID NO: 50 to carry out a PCR amplification reaction, with the bisulfate-treated HOXA9 gene or a fragment thereof in the biological sample as a template;
the detection of the methylation level of the PTGER4 gene comprises the use of a primer pair having the sequences as set forth in SEQ ID NOs: 55 and 56, a blocking primer having the sequence as set forth in SEQ ID NO: 57 and a probe having the sequence as set forth in SEQ ID NO: 58 to carry out a PCR amplification reaction, with the bisulfate-treated PTGER4 gene or a fragment thereof in the biological sample as a template;
the detection of the methylation level of the RARB gene comprises the use of a primer pair having the sequences as set forth in SEQ ID NOs: 63 and 64, a blocking primer having the sequence as set forth in SEQ ID NO: 65 and a probe having the sequence as set forth in SEQ ID NO: 66 to carry out a PCR amplification reaction, with the bisulfate-treated RARB gene or a fragment thereof in the biological sample as a template;
the detection of the methylation level of the RASSF1A gene comprises the use of a primer pair having the sequences as set forth in SEQ ID NOs: 75 and 76, a blocking primer having the sequence as set forth in SEQ ID NO: 77 and a probe having the sequence as set forth in SEQ ID NO: 78 to carry out a PCR amplification reaction, with the bisulfate-treated RASSF1A gene or a fragment thereof in the biological sample as a template;
the detection of the methylation level of the Septin9 gene comprises the use of a primer pair having the sequences as set forth in SEQ ID NOs: 83 and 84, a blocking primer having the sequence as set forth in SEQ ID NO: 85 and a probe having the sequence as set forth in SEQ ID NO: 86 to carry out a PCR amplification reaction, with the bisulfate-treated Septin9 gene or a fragment thereof in the biological sample as a template; and
the detection of the methylation level of the SHOX2 gene comprises the use of a primer pair having the sequences as set forth in SEQ ID NOs: 91 and 92, a blocking primer having the sequence as set forth in SEQ ID NO: 93 and a probe having the sequence as set forth in SEQ ID NO: 94 to carry out a PCR amplification reaction, with the bisulfate-treated SHOX2 gene or a fragment thereof in the biological sample as a template, wherein the probes have a fluorescent group at one end and a fluorescence quenching group at the other end.

6. The method of claim 1, wherein the method further comprises using a primer pair having sequences as set forth in SEQ ID NOs: 99 and 100 and a probe having the sequence as set forth in SEQ ID NO: 101 to carry out a PCR amplification reaction, with a bisulfate-treated ACTB gene or a fragment thereof used as an internal reference gene in the biological sample as a template.

7. The method of claim 1, wherein the detection of the methylation level of the BCAT1 gene comprises the use of a primer pair having the sequences as set forth in SEQ ID NOs:11 and 12, a blocking primer having the sequence as set forth in SEQ ID NO:13 and a probe having the sequence as set forth in SEQ ID NO:14 to carry out a PCR amplification reaction, with the bisulfate-treated BCAT1 gene or a fragment thereof in the biological sample as a template; the detection of the methylation level of the CDH1 gene comprises the use of a primer pair having the sequences as set forth in SEQ ID NOs:19 and 20, a blocking primer having the sequence as set forth in SEQ ID NO:21 and a probe having the sequence as set forth in SEQ ID NO:22 to carry out a PCR amplification reaction, with the bisulfate-treated CDH1 gene or a fragment thereof in the biological sample as a template; the detection of the methylation level of the HOXA9 gene comprises the use of a primer pair having the sequences as set forth in SEQ ID NOs:47 and 48, a blocking primer having the sequence as set forth in SEQ ID NO:49 and a probe having the sequence as set forth in SEQ ID NO:50 to carry out a PCR amplification reaction, with the bisulfate-treated HOXA9 gene or a fragment thereof in the biological sample as a template; the detection of the methylation level of the RASSF1A gene comprises the use of a primer pair having the sequences as set forth in SEQ ID NOs:75 and 76, a blocking primer having the sequence as set forth in SEQ ID NO:77 and a probe having the sequence as set forth in SEQ ID NO:78 to carry out a PCR amplification reaction, with the bisulfite-treated RASSF1A gene or a fragment thereof in the biological sample as a template; and the detection of the methylation level of the SHOX2 gene comprises the use of a primer pair having the sequences as set forth in SEQ ID NOs:91 and 92, a blocking primer having the sequence as set forth in SEQ ID NO:93 and a probe having the sequence as set forth in SEQ ID NO:94 to carry out a PCR amplification reaction, with the bisulfite-treated SHOX2 gene or a fragment thereof in the biological sample as a template.

* * * * *

UNITED STATES PATENT AND TRADEMARK OFFICE
CERTIFICATE OF CORRECTION

| | |
|---|---|
| PATENT NO. | : 12,018,333 B2 |
| APPLICATION NO. | : 16/964159 |
| DATED | : June 25, 2024 |
| INVENTOR(S) | : Mingming Li et al. |

Page 1 of 2

It is certified that error appears in the above-identified patent and that said Letters Patent is hereby corrected as shown below:

In the Specification

| | | | |
|---|---|---|---|
| | Column 4, | Line 52, | change "bisulfate-treated" to --bisulfite-treated-- |
| | Column 12, | Line 44, | change "RARE, RASSF1A," to --RARB, RASSF1A,-- |
| | Column 15, | Line 62, | change "a bisulfate reagent." to --a bisulfite reagent.-- |
| | Column 16, | Line 6, | change "bisulfate reagents," to --bisulfite reagents,-- |
| | Column 16, | Line 43, | change "100 μL magnetic" to --100 μl magnetic-- |
| | Column 17, | Line 60, | change "BARB, RASSF1A," to --RARB, RASSF1A,-- |
| | Column 17, | Line 62, | change "bisulfate-treated" to --bisulfite-treated-- |
| | Column 18, | Line 8, | change "BARB, RASSF1A," to --RARB, RASSF1A,-- |
| | Column 28, | Line 17, | change "valueswere combined" to --values were combined-- |

In the Claims

| | | | |
|---|---|---|---|
| Claim 1, | Column 63, | Line 46, | change "bisulfate-treated BCAT1" to --bisulfite-treated BCAT1-- |
| Claim 1, | Column 63, | Line 53, | change "bisulfate-treated DCLK1" to --bisulfite-treated DCLK1-- |
| Claim 1, | Column 63, | Line 67, | change "bisulfate-treated RASSF1A" to --bisulfite-treated RASSF1A-- |
| Claim 1, | Column 64, | Line 32, | change "bisulfate-treated Septin9" to --bisulfite-treated Septin9-- |
| Claim 1, | Column 64, | Line 40, | change "bisulfate-treated SHOX2" to --bisulfite-treated SHOX2-- |
| Claim 4, | Column 64, | Line 57, | change "bisulfate-treated BCAT1" to --bisulfite-treated BCAT1-- |
| Claim 4, | Column 65, | Line 3, | change "bisulfate-treated DCLK1" to |

Signed and Sealed this
Thirteenth Day of August, 2024

Katherine Kelly Vidal
*Director of the United States Patent and Trademark Office*

CERTIFICATE OF CORRECTION (continued)
U.S. Pat. No. 12,018,333 B2

| | | | |
|---|---|---|---|
| Claim 4, | Column 65, | Line 9, | change "bisulfate-treated FOXL2" to --bisulfite-treated FOXL2-- |
| Claim 4, | Column 65, | Line 15, | change "with the bisulfate-treated" to --with the bisulfite-treated-- |
| Claim 4, | Column 65, | Line 23, | change "bisulfate-treated PTGER4" to --bisulfite-treated PTGER4-- |
| Claim 4, | Column 65, | Line 29, | change "bisulfate-treated RARB" to --bisulfite-treated RARB-- |
| Claim 4, | Column 65, | Line 35, | change "with the bisulfate-treated" to --with the bisulfite-treated-- |
| Claim 4, | Column 65, | Line 42, | change "bisulfate-treated Septin9" to --bisulfite-treated Septin9-- |
| Claim 4, | Column 65, | Line 48, | change "bisulfate-treated SHOX2" to --bisulfite-treated SHOX2-- |
| Claim 5, | Column 65, | Line 60, | change "bisulfate-treated BCAT1" to --bisulfite-treated BCAT1-- |
| Claim 5, | Column 66, | Line 1, | change "bisulfate-treated CDH1" to --bisulfite-treated CDH1-- |
| Claim 5, | Column 66, | Line 9, | change "bisulfate-treated DCLK1" to --bisulfite-treated DCLK1-- |
| Claim 5, | Column 66, | Line 18, | change "bisulfate-treated FOXL2" to --bisulfite-treated FOXL2-- |
| Claim 5, | Column 66, | Line 26, | change "bisulfate-treated HOXA9" to --bisulfite-treated HOXA9-- |
| Claim 5, | Column 66, | Line 34, | change "bisulfate-treated PTGER4" to --bisulfite-treated PTGER4-- |
| Claim 5, | Column 66, | Line 43, | change "bisulfate-treated RARB" to --bisulfite-treated RARB-- |
| Claim 5, | Column 66, | Line 51, | change "bisulfate-treated RASSF1A" to --bisulfite-treated RASSSF1A-- |
| Claim 5, | Column 66, | Line 60, | change "bisulfate-treated Septin9" to --bisulfite-treated Septin9-- |
| Claim 5, | Column 67, | Line 1, | change "bisulfate-treated SHOX2" to --bisulfite-treated SHOX2-- |
| Claim 6, | Column 67, | Line 9, | change "bisulfate-treated ACTB" to --bisulfite-treated ACTB-- |
| Claim 7, | Column 67, | Line 19, | change "bisulfate-treated BCAT1" to --bisulfite-treated BCAT1-- |
| Claim 7, | Column 67, | Line 27, | change "bisulfate-treated CDH1" to --bisulfite-treated CDH1-- |
| Claim 7, | Column 68, | Line 8, | change "bisulfate-treated HOXA9" to --bisulfite-treated HOXA9-- |